(12) United States Patent
Blackbeard et al.

(10) Patent No.: US 10,292,793 B2
(45) Date of Patent: May 21, 2019

(54) ANGULATED DENTAL IMPLANT

(71) Applicant: Southern Implants (PTY) Ltd, Irene, Centurion (ZA)

(72) Inventors: Graham Alan Blackbeard, Centurion (ZA); Leith Carruthers Cumming, Centurion (ZA)

(73) Assignee: Southern Implants (PTY) Ltd, Irene, Centurion (ZA)

( * ) Notice: Subject to any disclaimer, the term of this patent is extended or adjusted under 35 U.S.C. 154(b) by 0 days.

(21) Appl. No.: 15/446,132

(22) Filed: Mar. 1, 2017

(65) Prior Publication Data

US 2017/0281320 A1 Oct. 5, 2017

Related U.S. Application Data

(60) Provisional application No. 62/361,665, filed on Jul. 13, 2016, provisional application No. 62/315,274, filed on Mar. 30, 2016.

(51) Int. Cl.
*A61C 8/00* (2006.01)

(52) U.S. Cl.
CPC ............ *A61C 8/0056* (2013.01); *A61C 8/006* (2013.01); *A61C 8/0022* (2013.01);
(Continued)

(58) Field of Classification Search
CPC ... A61C 8/0022; A61C 8/0025; A61C 8/0034; A61C 8/0037; A61C 8/0054;
(Continued)

(56) References Cited

U.S. PATENT DOCUMENTS 5,564,926 A * 10/1996 Brånemark ............ A61C 8/003
433/173
5,573,401 A * 11/1996 Davidson ................. A61C 7/12
433/173
(Continued)

FOREIGN PATENT DOCUMENTS

BR MU8 700 304 U2 4/2009
BR MU8700304 * 4/2009 ........... A61C 13/263
(Continued)

OTHER PUBLICATIONS

Stolyarov, V.V. et al., "Microstructure and properties of pure Ti processed by ECAP and cold extrusion," Materials Science and Engineering A303 (2001), pp. 82-89 (8 pages).
(Continued)

*Primary Examiner* — Matthew M Nelson
(74) *Attorney, Agent, or Firm* — Nixon Peabody LLP

(57) ABSTRACT

A dental implant includes a generally cylindrical body, an interior bore, and a non-rotational feature. The generally cylindrical body has a main-central axis and is formed from cold-worked, high strength, commercially pure titanium having an ultimate tensile strength of at least about 900 MPa. The generally cylindrical body has a proximal portion and an opposing distal portion for anchoring the dental implant in bone of a patient. The interior bore is formed in the generally cylindrical body and has (i) a bore-central axis and (ii) a threaded portion for receiving a screw that is configured to removable hold an abutment in engagement with the dental implant. The non-rotational feature is configured to engage the abutment in a non-rotational fashion.

12 Claims, 15 Drawing Sheets

(52) U.S. Cl.
CPC .......... *A61C 8/0025* (2013.01); *A61C 8/0034* (2013.01); *A61C 8/0037* (2013.01); *A61C 8/0054* (2013.01); *A61C 8/0068* (2013.01); *A61C 8/0074* (2013.01); *A61C 8/0089* (2013.01)

(58) Field of Classification Search
CPC ..... A61C 8/0056; A61C 8/006; A61C 8/0068; A61C 8/0074; A61C 8/0089
USPC .................................................. 433/172–176
See application file for complete search history.

(56) References Cited

U.S. PATENT DOCUMENTS

| | | | |
|---|---|---|---|
| 2012/0178048 A1 | 7/2012 | Cottrell | |
| 2014/0087331 A1* | 3/2014 | Hildmann | A61C 8/0025 433/174 |
| 2014/0272794 A1* | 9/2014 | Legum | A61C 8/0013 433/174 |
| 2016/0015483 A1* | 1/2016 | Kumar | A61C 8/0012 606/301 |

FOREIGN PATENT DOCUMENTS

| | | | | |
|---|---|---|---|---|
| CN | 201727594 U | 2/2011 | | |
| WO | WO 2008/157137 A1 | 12/2008 | | |
| WO | WO 2008157137 A1 * | 12/2008 | ............ | A61C 8/005 |
| WO | WO 2012/007118 A1 | 1/2012 | | |
| WO | WO 2015/162612 A1 | 10/2015 | | |
| WO | WO 2016/033642 A1 | 3/2016 | | |

OTHER PUBLICATIONS

International Preliminary Report on Patentability in International Application No. PCT/IB2017/051211, dated Jun. 13, 2018 (27 pages).

International Search Report and Written Opinion of International Searching Authority for PCT/IB2017/051211, dated May 15, 2017 (20 pages).

* cited by examiner

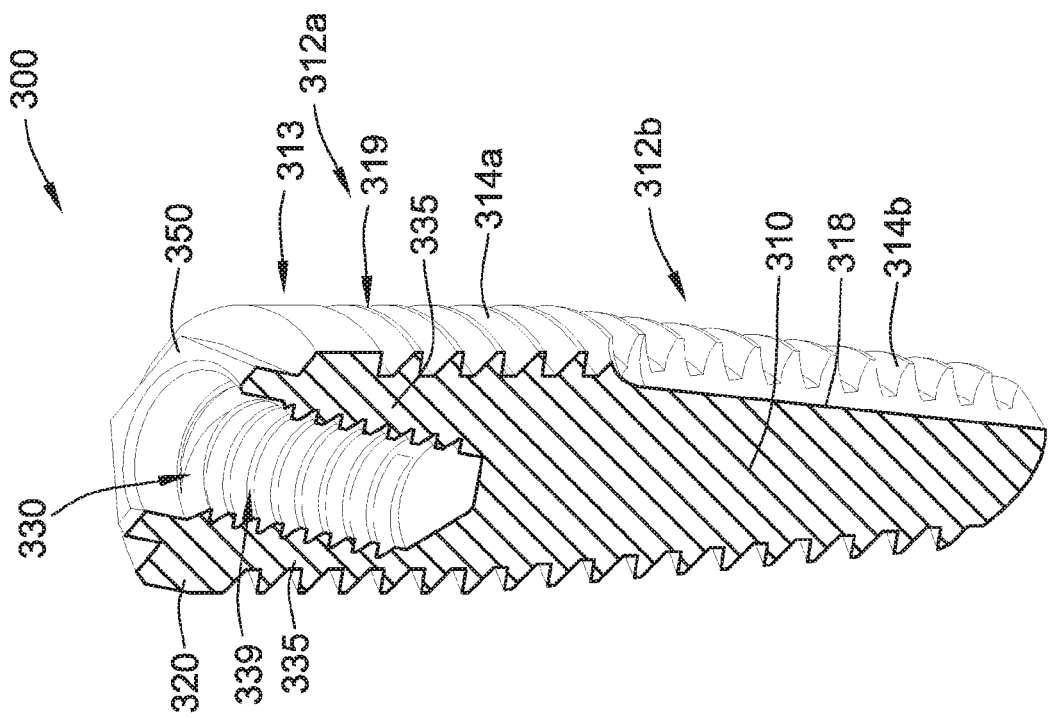
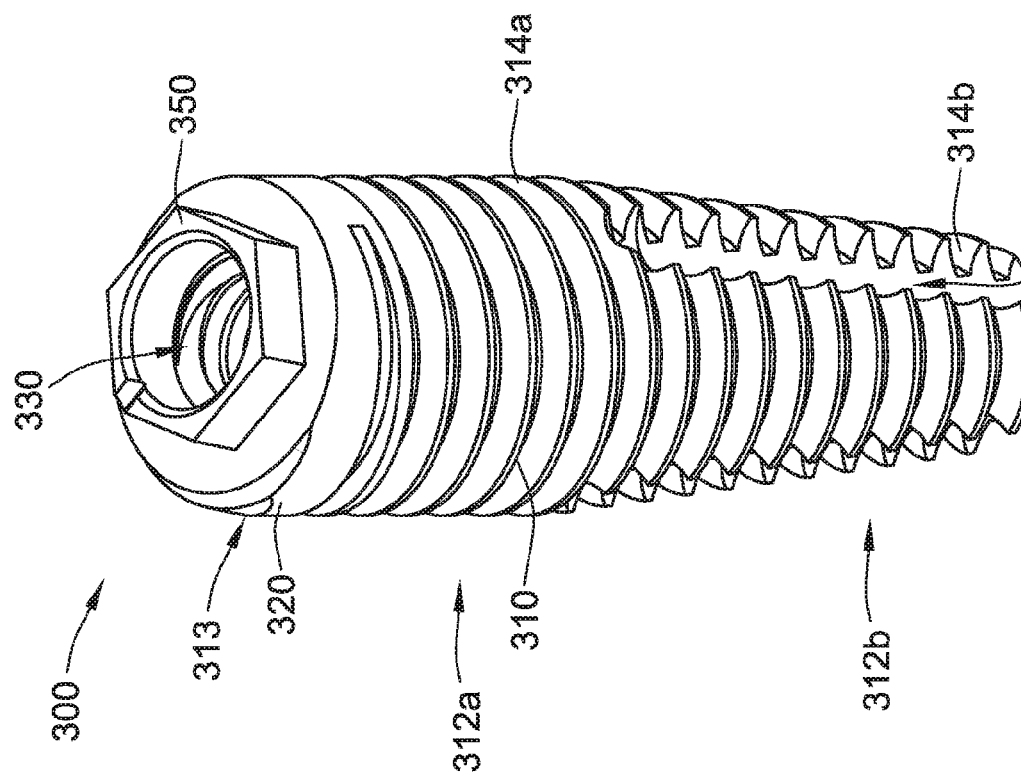

ANGULATED DENTAL IMPLANT

CROSS-REFERENCE TO RELATED APPLICATIONS

This application claims the benefit of and priority to U.S. Provisional Application No. 62/315,274, filed Mar. 30, 2016, and U.S. Provisional Application No. 62/361,665, filed Jul. 13, 2016, each of which is hereby incorporated by reference herein in its entirety.

TECHNICAL FIELD

This disclosure relates to restorative dental implants and abutments and more specifically to dental implants formed from cold-worked, high strength, commercial pure titanium.

BACKGROUND

Single tooth restorations (e.g., crowns) present the unique requirement that they must be supported non-rotationally on an underlying structure (e.g., a natural tooth prep, an abutment/implant assembly, etc.). When the underlying structure is a prepared natural tooth, this non-rotational supporting requirement is met in the normal course of preparing the natural tooth with a non-circular cross-section. Similarly, when the underlying structure is an abutment secured to a dental implant, this non-rotational supporting requirement is met by preparing and/or using an abutment with a noncircular cross-section. This latter scenario can be more complicated due to the added connection between the dental implant and the abutment.

Typically, a dental implant is implanted into bone of a patient's jaw (e.g., maxilla and/or mandible). While numerous design iterations have been marketed, overall there have been two types of dental implant-abutment interfaces within these assemblies: (i) an external-connection dental implant and (ii) an internal-connection dental implant. The external-connection dental implant design typically includes a hexagonal boss (or another anti-rotation feature) protruding out of the dental implant's upper surface, whereas the internal-connection dental implant design typically includes a hexagonal socket (or another anti-rotation feature) extending down and into the dental implant's upper portion. With either dental implant (e.g., external/boss or internal/socket), a corresponding abutment engages the dental implant in a non-rotational fashion and is typically secured thereto with a screw.

In most restorative situations, a central or main axis of the tooth restoration and/or of the post of the abutment is at a non-zero angle relative to the central or main axis of the dental implant. This is typically the case due to the natural anatomy of most patients. As such, when installed, natural forces (e.g., from chewing) generated in the mouth are transferred from the tooth restoration (e.g., crown), to the abutment, and then to the dental implant installed in the patient's jawbone. Because of the angle between the central axis of the tooth restoration and the central axis dental implant, the forces also create bending moments that can cause the abutment and dental implant to separate, which can allow leakage into the dental implant.

One solution to mitigating the negative impact of such forces on the connection site between the abutment and the dental implant involves the use of angled dental implants. Angled dental implants typically include an angled mating surface (e.g., angled relative to horizontal) for connection with the abutment and an angled threaded bore (e.g., angled relative to vertical) for receiving the screw that holds the abutment to the dental implant at an angle relative to a central or main axis of the dental implant. While such angled dental implants aid in mitigating the negative impact of the natural forces at the connection site (between the abutment and the dental implant), the inclusion of such internal angled features within the dental implant generally requires the dental implant to have a relatively larger sized outer diameter to accommodate such angled features therein (e.g., a 6 millimeter outer diameter). More specifically, the inclusion of such internal angled features can cause a portion of an outer wall of the angled dental implant to have thickness that is much thinner than the rest of the wall forming the angled dental implant. As such, if the outer diameter is too small (even if just at a relatively small portion of the angled dental implant), the angled dental abutment may be prone to easily break/snap/fail. Due to these limitations, angled dental implants have typically been limited to having at least a 4.5 millimeter outer diameter; however, such angled dental implants are not typically suitable for use in the anterior maxilla/mandible as the anterior maxilla/mandible in many patients is not able to support dental implants with such a large outer diameter.

Thus, a need exists for angled dental implants with relatively smaller outer diameters (e.g., 3.0 mm, 3.25 mm, 3.5 mm, 4.0 mm, etc.) for use, for example, in the anterior maxilla/mandible of a patient. The present disclosure is directed to solving these problems and addressing other needs.

BRIEF SUMMARY

According to some implementations of the present disclosure, a dental implant includes a generally cylindrical body, an interior bore, and a non-rotational feature. The generally cylindrical body has a main-central axis and is formed from cold-worked, high strength, commercially pure titanium having an ultimate tensile strength of at least about 800 MPa, preferably at least about 900 MPa, such as, for example, 920 MPa. The generally cylindrical body has a proximal portion and an opposing distal portion for anchoring the dental implant in bone of a patient. The interior bore is formed in the generally cylindrical body and has (i) a bore-central axis and (ii) a threaded portion for receiving a screw that is configured to removable hold an abutment in engagement with the dental implant. The non-rotational feature is configured to engage the abutment in a non-rotational fashion.

According to some implementations of the present disclosure, an angled dental implant includes a generally cylindrical body, an interior bore, and non-rotational feature. The generally cylindrical body has a maximum outer diameter and a main-central axis. The generally cylindrical body is formed from cold-worked, high strength, commercially pure titanium having an ultimate tensile strength of at least about 900 MPa. The generally cylindrical body has a proximal portion and an opposing distal portion for anchoring the angled dental implant in bone of a patient. The interior bore is formed in the generally cylindrical body, thereby forming a circumferentially extending wall defined by at least a portion of an outer surface of the generally cylindrical body and at least a portion of an inner surface of the interior bore. The interior bore has a bore-central axis that is at an angle between about 7° degrees and about 31° degrees relative to the main-central axis of the generally cylindrical body. The relative angle of the bore-central axis causes at least a first portion of the circumferentially extending wall to have a varying thickness about a circumference of the first portion. The thickness of the circumferentially extending wall at the first portion varies from a thinnest portion adjacent to a first side of the generally cylindrical body to a thickest portion adjacent to a second opposing side of the generally cylindrical body. The interior bore has a threaded portion for receiving a screw configured to removable hold an abutment in engagement with the angled dental implant. The non-rotational feature is configured to engage the abutment in a non-rotational fashion. A ratio of the maximum outer diameter of the generally cylindrical body to the thinnest portion of the circumferentially extending wall adjacent to the first side of the generally cylindrical body at the first portion is between about 16 and about 80.

A method of making a dental implant includes machining cold-worked commercially pure titanium into a generally cylindrical body having a main-central axis. The generally cylindrical body has a proximal portion and an opposing distal portion for anchoring the dental implant in bone of a patient. The cold-worked commercially pure titanium has an ultimate tensile strength of at least about 900 MPa. An interior bore is formed in the generally cylindrical body. The interior bore includes (i) a bore-central axis and (ii) a threaded portion. A non-rotational feature is formed in the generally cylindrical body for engaging an abutment.

According to some implementations of the present disclosure, an angled zygomatic dental implant includes a generally cylindrical body, an interior bore, and a non-rotational feature. The generally cylindrical body has a maximum outer diameter and a main-central axis. The generally cylindrical body is formed from cold-worked, high strength, commercially pure titanium having an ultimate tensile strength of at least about 900 MPa. The generally cylindrical body has a proximal portion, a middle portion, and a threaded distal portion for anchoring the angled zygomatic dental implant in bone of a patient. The generally cylindrical body has a length between about 25 millimeters and about 60 millimeters. The interior bore is formed in the generally cylindrical body, thereby forming a circumferentially extending wall defined by at least a portion of an outer surface of the generally cylindrical body and at least a portion of an inner surface of the interior bore. The interior bore has a bore-central axis that is at an angle between about 40° and about 65° relative to the main-central axis of the generally cylindrical body. The relative angle of the bore-central axis causes the circumferentially extending wall to have a thinnest portion. The interior bore has a threaded portion for receiving a screw configured to removable hold an abutment in engagement with the angled zygomatic dental implant. The non-rotational feature is configured to engage the abutment in a non-rotational fashion. A ratio of the maximum outer diameter of the generally cylindrical body to the thinnest portion of the circumferentially extending wall is between about 50 and about 75.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

FIG. 3A is a perspective view of an angled-bore dental implant with an external-connection according to some implementations of the present disclosure;
FIG. 3B is a perspective cutaway view of the dental implant shown in FIG. 3A.

Figure 1B:
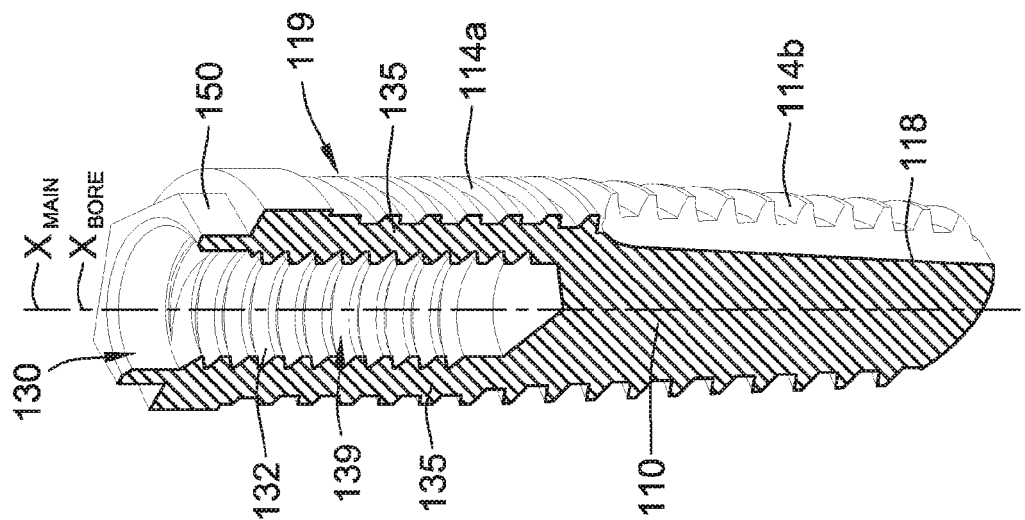
FIG. 1B is a perspective cutaway view of the dental implant shown in FIG. 1A.

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

The dental implants of the present disclosure described herein are formed from (e.g., machined out of) cold-worked, high strength, commercially pure titanium having an ultimate tensile strength of at least about 900 megapascals (MPa). Ultimate tensile strength it is meant to refer to the maximum stress that a material can withstand while being stretched or pulled before breaking. By cold-worked, it is meant that the material is shaped at a temperature below its recrystallization temperature (e.g., ambient temperature). Examples of such shaping techniques include: squeezing, bending, drawing, shearing, rolling, or any combinations thereof.

In some implementations, the dental implants of the present disclosure are formed from cold-worked, high strength, commercially pure titanium having an ultimate tensile strength of at least about 900 megapascals (MPa). The material used to make the dental implants of the present disclosure starts as commercially pure titanium (e.g., Grade IV Titanium as defined by the ASTM International standard ASTM F67) with a relatively lower ultimate tensile strength (e.g., 550 MPa). Then, the commercially pure titanium is cold worked, which increases the commercially pure titanium's ultimate tensile strength from its initial value to a relatively higher value (e.g., 800 MPa, 850 MPa, 900 MPa, 920 MPa, 940 MPa, 960 MPa, etc.). Then, the dental implants of the present disclosure are machined out of this cold worked, high strength, commercially pure titanium material having the relatively higher ultimate tensile strength (e.g., 920 MPa). As such, the dental implants of the present disclosure are able to be machined with relatively smaller sizes (e.g., smaller diameters) without potentially sacrificing long term performance of the dental implants compared with dental implants machined out of materials having relatively lower ultimate tensile strength (e.g., 400 MPa).

Figure 1A:
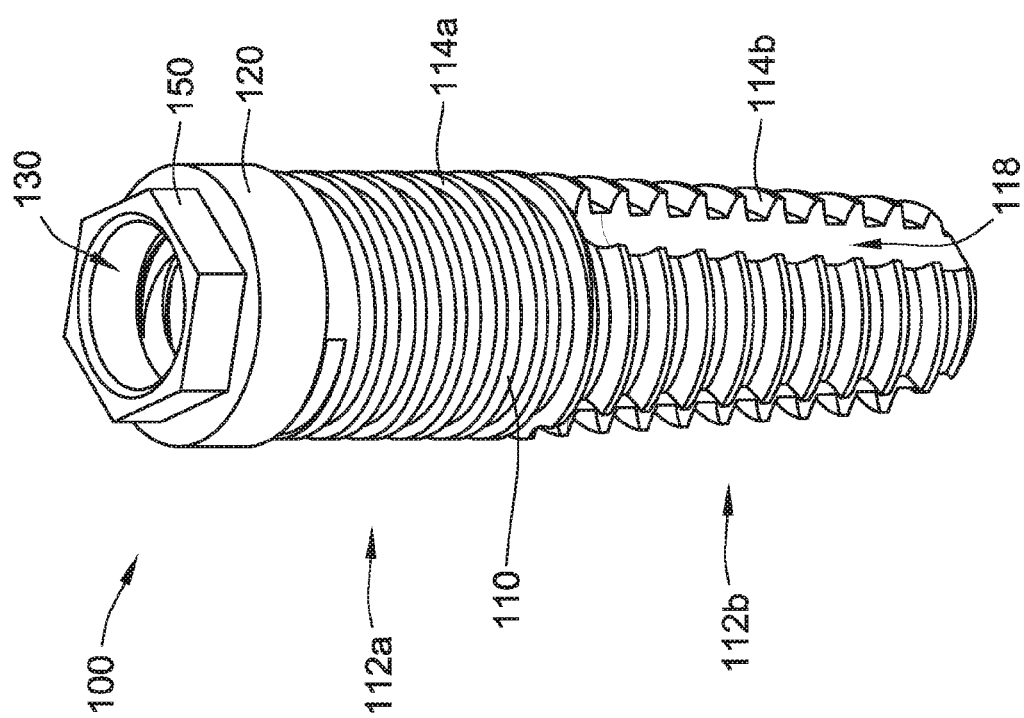
FIG. 1A is a perspective view of a straight-bore dental implant with an external-connection according to some implementations of the present disclosure.
Figure 1C:
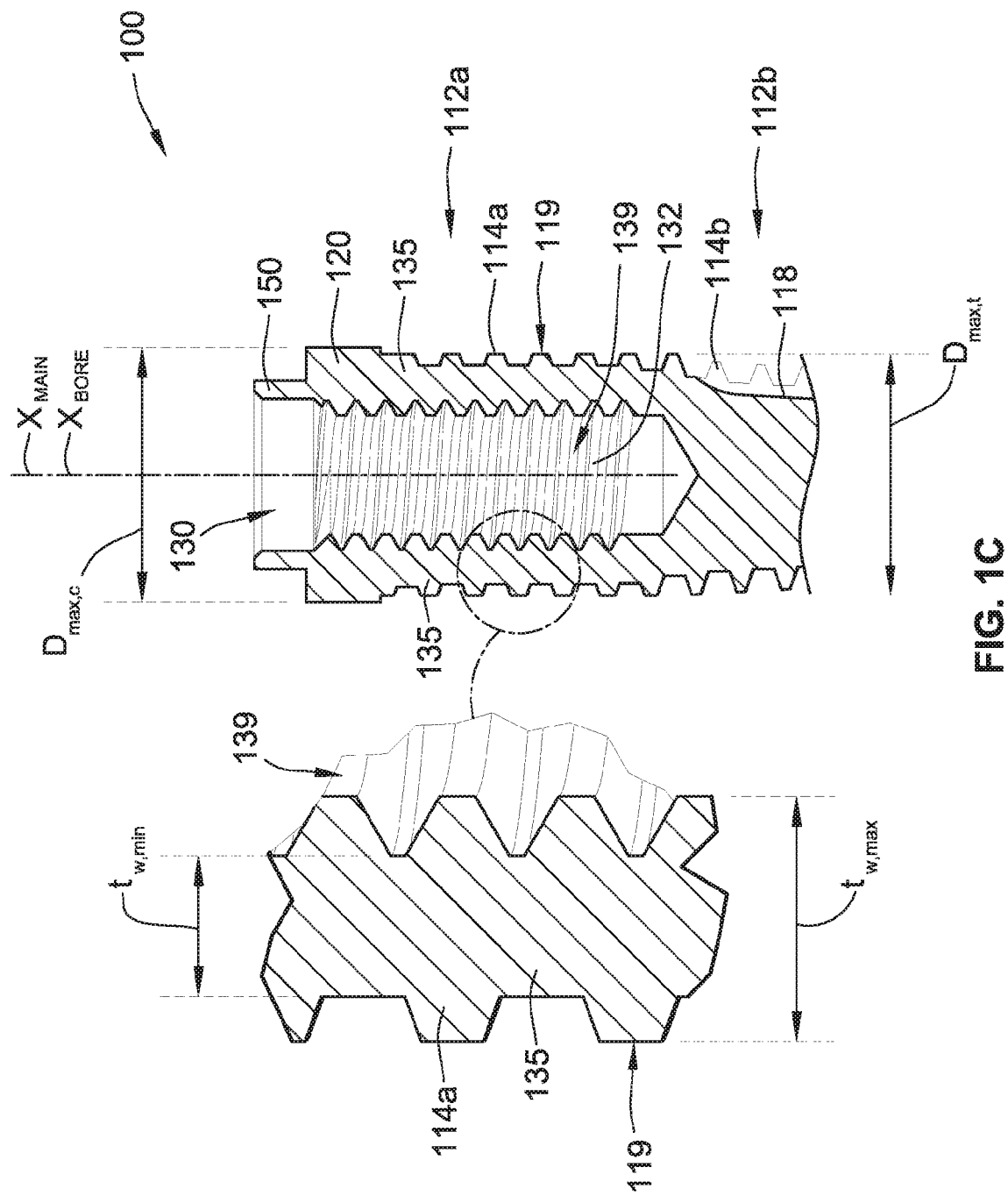
FIG. 1C is a partial cross-sectional view of the dental implant shown in FIG. 1A.

Referring generally to FIGS. 1A-1C, a dental implant 100 includes a generally cylindrical body 110, an interior bore 130, and a non-rotational feature 150. The generally cylindrical body 110 is generally divided into an upper or proximal portion 112a and a lower or distal portion 112b. The distal portion 112b is typically for anchoring the dental implant 100 in bone of a patient. For example, the dental implant 100 can be anchored into a patient's maxilla or mandible.

The proximal portion 112a includes first threads 114a about an exterior surface thereof and the distal portion 112b includes second threads 114b about an exterior surface thereof. In some implementations, the first and second threads 114a,b are the same (e.g., same pitch, same cross-section, and/or same number of starts, etc.) and in some alternatives, the first and the second threads 114a,b are different. For example, the first threads 114a can be a multi-lead thread with three threads each having a pitch of 0.6 millimeters (e.g., 0.2 millimeters between adjacent turns of the multi-lead threads) and the second thread 114b can be a single thread having a pitch of 0.6 millimeters. Various alternative threads, pitches, and ratios are contemplated, such as multi-lead threads on both the first threads 114a and the second threads 114b with the same or different pitches. The first and second threads 114a,b can be blended together (e.g., near the middle of the dental implant 100) or separate and distinct (e.g., not touching). In some implementations, the first thread 114a (about the distal portion 112b) is a micro thread 114a and the second thread 114b (about the proximal portion 112b) is a main thread 114b in that the main thread 114b is for deeper, primary engagement with the bone. In such implementations, the micro thread 114a has a smaller peak-to-trough distance and a larger minor thread diameter as compared with the peak-to-trough distance and minor thread diameter of the main thread 114b. In some exemplary implementations, the peak-to-trough distance of the first thread is in the range from about 0.05 millimeters to 0.1 millimeters and the peak-to-trough distance of the second thread is in the range from about 0.2 millimeters to about 0.5 millimeters. For example, peak-to-trough distance of the first thread is about 0.075 millimeters and the peak-to-trough distance of the second thread is about 0.25 millimeters.

The distal portion 112b of the generally cylindrical body 110 includes three generally vertical flutes 118 spaced about the circumference of the dental implant 100 that cross (e.g., break up) the second thread 114b. The flutes 118 aid the installation of the dental implant 100 by (i) self-tapping the dental implant 100 into the patient's bone socket and/or (ii) providing a path for material to be ejected from the cavity (e.g., bone socket) receiving the dental implant 100 during installation. More or fewer flutes 118 are also contemplated (e.g., one, two, four, five, etc.).

The proximal portion 112a of the generally cylindrical body 110 also includes a collar section 120. The collar section 120 is generally cylindrical and is positioned near and/or at a proximal end of the dental implant 100. The collar section 120 is distinct from the rest of the proximal portion 112a of the generally cylindrical body 110 as the collar section 120 does not include the first thread 114a therearound. As shown in FIGS. 1A-1C, the collar section 120 has a maximum outer diameter $D_{max,c}$ that is slightly larger than the maximum outer diameter $D_{max,t}$ of the rest of the proximal portion 112a, which is defined by the outer diameter of the first thread 114a. Alternatively, the maximum outer diameter $D_{max,c}$ of the collar section 120 is equal to or less than the maximum outer diameter $D_{max,t}$ of the first thread 114a.

Throughout the present disclosure, reference is made to various sized dental implants. To identify the various dental implants of the present disclosure, the dental implants may be referred to as having a nominal size. For example, the nominal size may generally or nominally refer to a dental implant's maximum outer diameter or width. This maximum outer diameter can refer to the maximum outer diameter $D_{max,c}$ of the collar section 120 and/or the maximum outer diameter $D_{max,t}$ of the first thread 114a (as opposed to the inner diameter of the first thread 114a). By way of example, the dental implant 100 shown in FIGS. 1A-1C can be referred to as a 3.25 millimeter dental implant, which is the nominal maximum outer diameter $D_{max,c}$ of the collar section 120 and/or the nominal maximum outer diameter $D_{max,t}$ of the first thread 114a. By nominal, it is meant that the outer diameter $D_{max}$ is about 3.25 millimeters and not necessarily exactly 3.25 millimeters. By about 3.25 millimeters it is meant that the dimension has a tolerance of about plus or minus 0.1 millimeter.

The non-rotational feature 150 generally protrudes from the collar section 120 and is external to the interior bore 130 (e.g., at least to the threaded portion of the interior bore 130). As shown, the non-rotational feature 150 is a six-sided hexagonal boss that can non-rotationally mate with a corresponding non-rotational feature (e.g., non-rotational feature 685 shown in FIG. 6C) of an abutment (e.g., abutment 675 shown in FIGS. 6A-6C) in a non-rotational fashion. Various alternative non-rotational features are contemplated, such as, for example, a four-sided square or rectangular boss (not shown), a five-sided polygonal boss (not shown), a twelve-sided polygonal/star boss (not shown), a three-piece clover shaped boss (not shown), etc.

The generally cylindrical body 110 of the dental implant 100 has a main-central axis $X_{main}$. The main-central axis $X_{main}$ is defined as a straight axis/line that goes through the geometric center and/or the axis of symmetry of at least the distal portion 112b of the generally cylindrical body 110 of the dental implant 100. As shown in FIGS. 1A-1C, the main-central axis $X_{main}$ of the dental implant 100 also goes through the geometric center and/or the axis of symmetry of the proximal portion 112a of the generally cylindrical body 110 of the dental implant 100. This is because the dental implant 100 is a straight-bore dental implant as opposed to some of the angled-bore dental implants described herein.

The interior bore 130 is formed in the generally cylindrical body 110 of the dental implant 100. The interior bore 130 includes a female or internal thread 132 therein to threadingly mate with a screw (e.g., screw 690 shown in FIGS. 6B and 6C) to hold the abutment on the dental implant 100 (as best shown, for example, in FIG. 6C). The interior bore 130 has a bore-central axis $X_{bore}$. The bore-central axis $X_{bore}$ is defined as a straight axis/line that goes through the geometric center and/or the axis of symmetry of at least the interior bore 130 of the dental implant 100. As shown in FIGS. 1A-1C, the bore-central axis $X_{bore}$ of the interior bore 130 also goes through the geometric center and/or the axis of symmetry of the distal portion 112b of the generally cylindrical body 110 of the dental implant 100. This is because the dental implant 100 is a straight-bore dental implant as opposed to some of the angled-bore dental implants described herein. Alternatively, the bore-central axis $X_{bore}$ can be at an angle relative to the main-central axis $X_{main}$ between about 7° and about 31°. Exemplarily dental implants having such angled bore-central axes are shown in, for example, FIGS. 2A-5C, which are described below in greater detail.

The interior bore 130 forms a circumferentially extending wall 135 that is defined by an outer surface 119 of the generally cylindrical body 110 and an inner surface 139 of the interior bore 130. The circumferentially extending wall 135 has a minimum thickness $t_{w,min}$ and a maximum thickness $t_{w,max}$ as best shown in FIG. 1C. The minimum and maximum thicknesses $t_{w,min}$ and $t_{w,max}$ of the circumferentially extending wall 135 vary depending on the size of the dental implant 100 (e.g., a 3.0 diameter implant, a 3.25 diameter implant, a 3.5 diameter implant, a 4.0 diameter implant, a 5.0 diameter implant, etc.), the inner diameter of the interior bore 130 (which can vary depending on the type/size of screw being used to hold the abutment to the implant), the size (e.g., pitch) of the first thread 114a, the size (e.g., pitch) of the internal thread 132, and/or the angle of the bore-central axis $X_{bore}$ relative to the main-central axis $X_{main}$ (which in the case of the dental implant 100 is zero).

It is also noted that the minimum and maximum thicknesses $t_{w,min}$ and $t_{w,max}$ of the circumferentially extending wall 135 can also depend on the location (e.g., vertical position along a height of the dental implant) that the thicknesses are being measured. For example, for an angled dental implant, the minimum thickness $t_{w,min}$ of the circumferentially extending wall near or at the proximal end of the interior bore will be different than the minimum thickness $t_{w,min}$ of the circumferentially extending wall near or at the distal end of the interior bore. Additionally, the thickness of the circumferentially extending wall 135 varies about the circumference (e.g., rotational position about the main-central axis $X_{main}$) of the angled dental implant due to the interior bore being at an angle relative to the main-central axis $X_{main}$, which is described below and shown in FIGS. 2A-5C.

Based on the exemplary implementation shown in FIGS. 1A-1C of the dental implant 100, a ratio of the maximum outer diameter $D_{max,c}$ or $D_{max,t}$ (e.g., the nominal outer diameter of 3.25 millimeters) of the generally cylindrical body 110 to the thinnest portion (e.g., thickness $t_{w,min}$) of the circumferentially extending wall 135 of the generally cylindrical body 110 is 3.25 millimeters/0.5 millimeters, which equals 6.5.

Figure 2B:
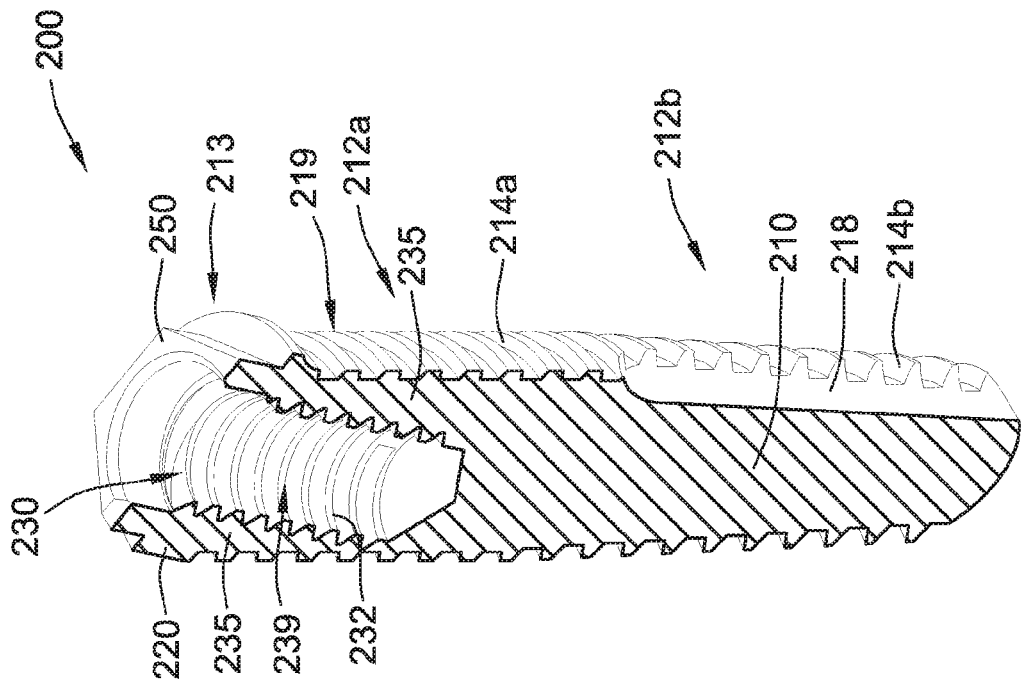
FIG. 2B is a perspective cutaway view of the dental implant shown in FIG. 2A.
Figure 2A:
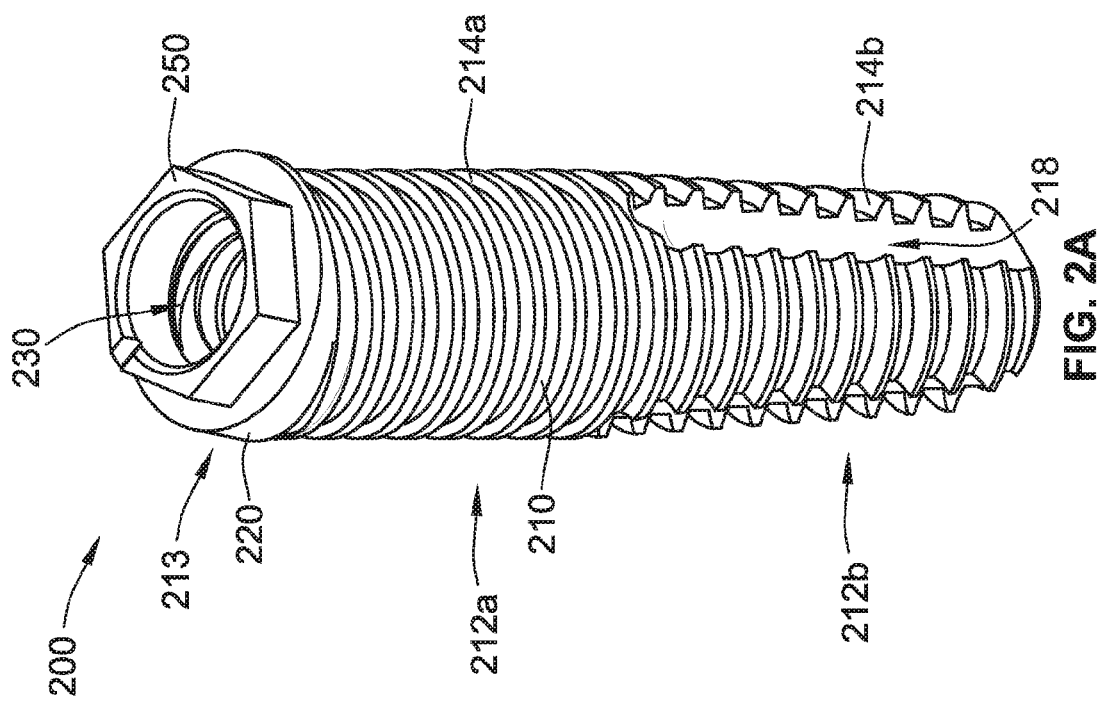
FIG. 2A is a perspective view of an angled-bore dental implant with an external-connection according to some implementations of the present disclosure.
Figure 2C:
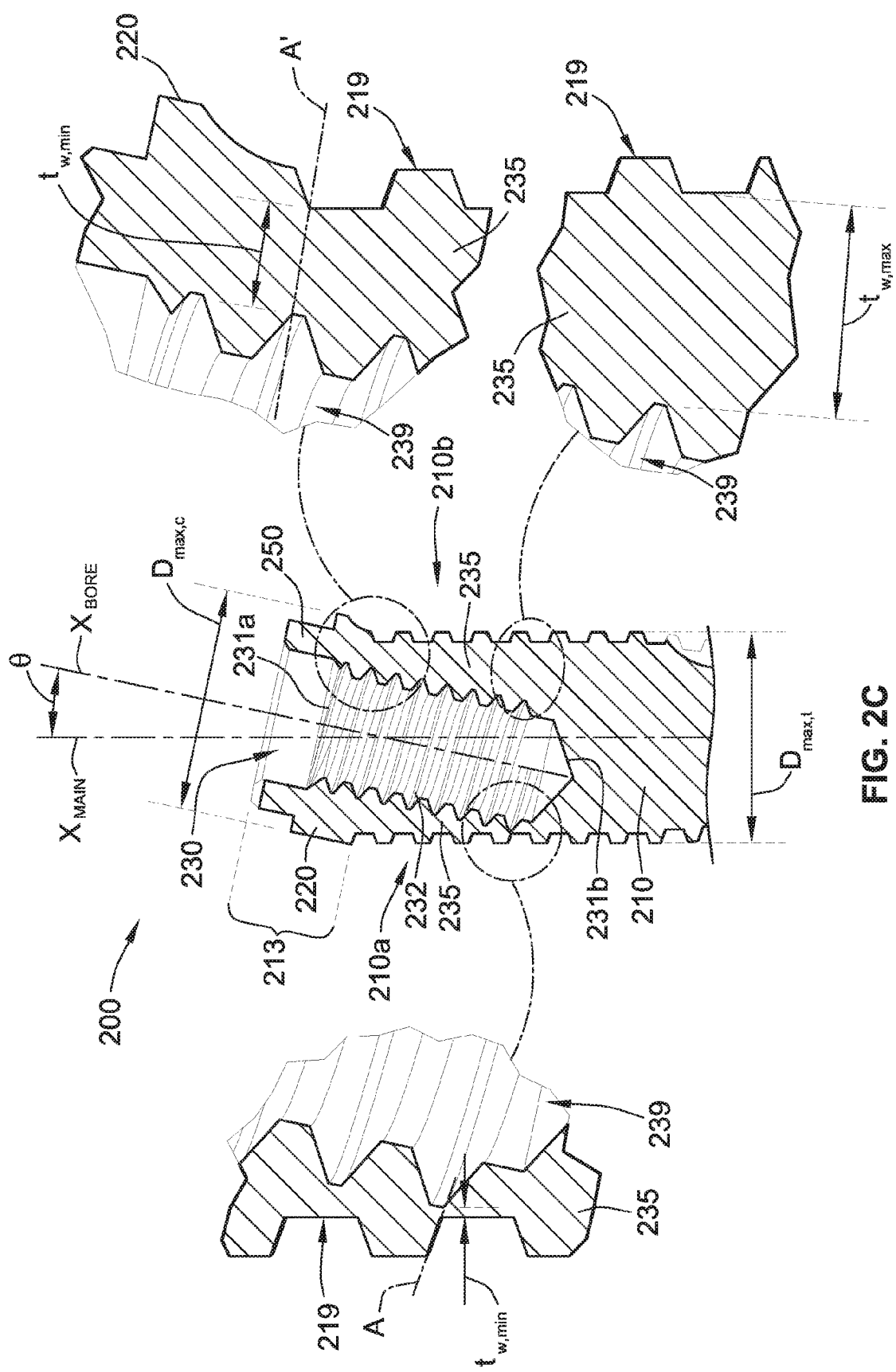
FIG. 2C is a partial cross-sectional view of the dental implant shown in FIG. 2A.

Now referring to FIGS. 2A-2C, an angled dental implant 200 having a generally cylindrical body 210 is shown that is similar to the dental implant 100 described herein and shown in FIGS. 1A-1C. However, the angled dental implant 200 generally differs from the dental implant 100 (FIGS. 1A-1C) in that a collar section 220 and an interior bore 230 of the angled dental implant 200 are angled relative to a main-central axis $X_{main}$ of the angled dental implant 200.

The angled dental implant 200 can be referred to as a 3.25 millimeter angled dental implant, which is the nominal maximum outer diameter $D_{max,c}$ of the collar section 220 and/or the nominal maximum outer diameter $D_{max,t}$ of a first thread 214a. The angled dental implant 200 further includes a non-rotational feature 250 that is the same as, or similar to, the non-rotational feature 150, except that the non-rotational feature 250 is angled relative to the main-central axis $X_{main}$ of the angled dental implant 200 as the non-rotational feature 250 extends from the angled collar section 220. Like the generally cylindrical body 110 of the dental implant 100, the generally cylindrical body 210 is generally divided into an upper or proximal portion 212a and a lower or distal portion 212b. The proximal portion 212a includes the first thread 214a and the distal portion 212b includes a second thread 214b that are the same as, or similar to, the first and second threads 114a,b. Moreover, the distal portion 212b includes three generally vertical flutes 218 that are the same as, or similar to, the flutes 118.

The generally cylindrical body 210 of the dental angled implant 200 has a main-central axis $X_{main}$. While the main-central axis $X_{main}$ of the angled dental implant 200 goes through the geometric center and/or the axis of symmetry of the distal portion 212b of the generally cylindrical body 210 (e.g., similar to the main-central axis $X_{main}$ of the dental implant 100), the main-central axis $X_{main}$ of the angled dental implant 200 does not go through (e.g., is not coincident with) the axis of symmetry of the proximal portion 212a of the generally cylindrical body 210. This is because the proximal portion 212a of the generally cylindrical body 210 of the angled dental implant 200 includes an angled portion 213 that is angled and/or offset relative to (1) the main-central axis $X_{main}$ of the angled dental implant 200 and (2) the rest of the generally cylindrical body 210 of the angled dental implant 200.

The proximal portion 212a includes the collar section 220, which differs from the collar section 120 of dental implant 100 in FIGS. 1A-1C in that the collar section 220 is angled relative to vertical and/or the main-central axis $X_{main}$ of the angled dental implant 200. The collar section 220 is generally cylindrical and is positioned near and/or at the proximal end of the angled dental implant 200.

The interior bore 230 is formed in the generally cylindrical body 210 of the angled dental implant 200. The interior bore 230 includes a female or internal thread 232 therein to threadingly mate with a screw (e.g., screw 690 shown in FIGS. 6B and 6C) to hold an abutment (e.g., abutment 675 shown in FIGS. 6A-6C) on the angled dental implant 200 (as best shown, for example, in FIG. 6C). The interior bore 230 has a bore-central axis $X_{bore}$. The bore-central axis $X_{bore}$ of the interior bore 230 goes through the geometric center and/or the axis of symmetry of the interior bore 230 of the angled dental implant 200. Unlike the dental implant 100 (FIGS. 1A-1C), the bore-central axis $X_{bore}$ of the interior bore 230 does not also go through the geometric center and/or the axis of symmetry of the distal portion 212b of the generally cylindrical body 210 of the angled dental implant 200. This is because the angled dental implant 200 is an angled-bore dental implant. As shown in FIG. 2C, the bore-central axis $X_{bore}$ of the interior bore 230 is at an angle θ relative to the main-central axis $X_{main}$ of the angled dental implant 200. The angle θ can be any angle, such as, for example, between about 7° and about 31° degrees. As shown in FIGS. 2A-2C, the angle θ is about 12°.

Similar to the interior bore 130, the interior bore 230 forms a circumferentially extending wall 235 that is defined by an outer surface 219 of the generally cylindrical body 210 and an inner surface 239 of the interior bore 230. The circumferentially extending wall 235 has a minimum thickness $t_{w,min}$ and a maximum thickness $t_{w,max}$ as best shown in FIG. 2C. The minimum and maximum thicknesses $t_{w,min}$ and $t_{w,max}$ of the circumferentially extending wall 235 vary depending on the size of the angled dental implant 200 (e.g., a 3.0 diameter implant, a 3.25 diameter implant, a 3.5 diameter implant, a 4.0 diameter implant, a 5.0 diameter implant, etc.), the inner diameter of the interior bore 230 (which can vary depending on the type/size of screw being used to hold the abutment to the implant), the size (e.g., pitch) of the first thread 114a, the size (e.g., pitch) of the internal thread 132, and/or the angle θ of the bore-central axis $X_{bore}$ relative to the main-central axis $X_{main}$ (which in the case of the angled dental implant 200 is about 12 degrees).

The minimum and maximum thicknesses $t_{w,min}$ and $t_{w,max}$ of the circumferentially extending wall 235 also depend on the location (e.g., vertical position along a height of the angled dental implant) that the thicknesses are being measured. For example, for the angled dental implant 200 in FIGS. 2A-2C, the minimum thickness $t_{w,min}$ of the circumferentially extending wall 235 near or at a proximal end 231a of the interior bore 230 is different than the minimum thickness $t_{w,min}$ of the circumferentially extending wall 235 near or at the distal end 231b of the interior bore 230. As an example, the angled dental implant 200 (shown in FIGS. 2A-2C), is a 3.25 diameter angled dental implant (nominal size) with an interior bore 230 having an angle θ of about 12 degrees. In this illustrated example, the minimum thickness $t_{w,min}$ of the circumferentially extending wall 235 at or near the distal end 231b (e.g., taken at line A) of the interior bore 230 is about 0.04 millimeters, which is adjacent to a first side 210a of the generally cylindrical body 210 of the angled dental implant 200. Similarly, the minimum thickness $t_{w,min}$ of the circumferentially extending wall 235 at or near the proximal end 231a (e.g., taken at line A') of the interior bore 230 is about 0.4 millimeters, which is adjacent to a second opposing side 210b of the generally cylindrical body 210 of the angled dental implant 200.

As can be appreciated by the above description and FIGS. 2A-2C, the thickness of the circumferentially extending wall 235 varies about the circumference (e.g., rotational position about the main-central axis $X_{main}$) of the angled dental implant 200 due to the interior bore 230 being at the angle θ relative to the main-central axis $X_{main}$. As best shown in FIG. 2C, for a horizontal cross-section of the generally cylindrical body 210 at or near the distal end 231b of the interior bore 230, the thickness of the circumferentially extending wall 235 varies about the circumference of the angled dental implant 200 from (1) the minimum thickness $t_{w,min}$ at or near the distal end 231b of the interior bore 230 adjacent to the first side 210a to (2) the maximum thickness $t_{w,max}$ at or near the distal end 231b of the interior bore 230 adjacent to the second opposing side 210b. As the horizontal cross-section of the generally cylindrical body 210 is moved vertically upward in FIG. 2C (i.e, towards the proximal end 231a of the interior bore 230), the thickness of the circumferentially extending wall 235 adjacent to the first and second sides 210a,b continues to vary until the horizontal cross-section of the generally cylindrical body 210 reaches and/or approaches the proximal end 231a where the minimum thickness $t_{w,min}$ flips from the first side 210a to the second opposing side 210b and similarly, the maximum thickness $t_{w,max}$ flips from the second opposing side 210b to the first side 210a.

In summary, the circumferentially extending wall 235 has one or more portions or sections that have a relatively thin thickness compared to the rest of the circumferentially extending wall 235. It is these portions of the circumferentially extending wall 235 that are more prone to breaking/failing/snapping when the angled dental implant 200 is loaded (e.g., coupled with an abutment and crown and used for mastication purposes in a patient's mouth). By machining the angled dental implant 200 out of the cold worked, commercially pure titanium material having the relatively higher ultimate tensile strength (e.g., 920 MPa) described herein, the angled dental implant 200 is able to have such relatively thin wall portions. As such, angled dental implants of the present disclosure are able to be machined with relatively smaller outer diameters and/or relatively larger angles θ as compared with previous dental implants and such relatively smaller angled dental implants can be used in areas of a patient's mouth requiring such smaller sized angled dental implants, such as, for example, the anterior maxilla and/or the anterior mandible.

Based on the exemplary implementation shown in FIGS. 2A-2C of the angled dental implant 200, a ratio of the maximum outer diameter $D_{max,c}$ or $D_{max,t}$ (e.g., the nominal outer diameter of 3.25 millimeters) of the generally cylindrical body 210 to the thinnest portion (e.g., thickness $t_{w,min}$) of the circumferentially extending wall 235 adjacent to the first side 210a of the generally cylindrical body 210 is 3.25 millimeters/0.04 millimeters, which equals 81.25.

Figure 3C:
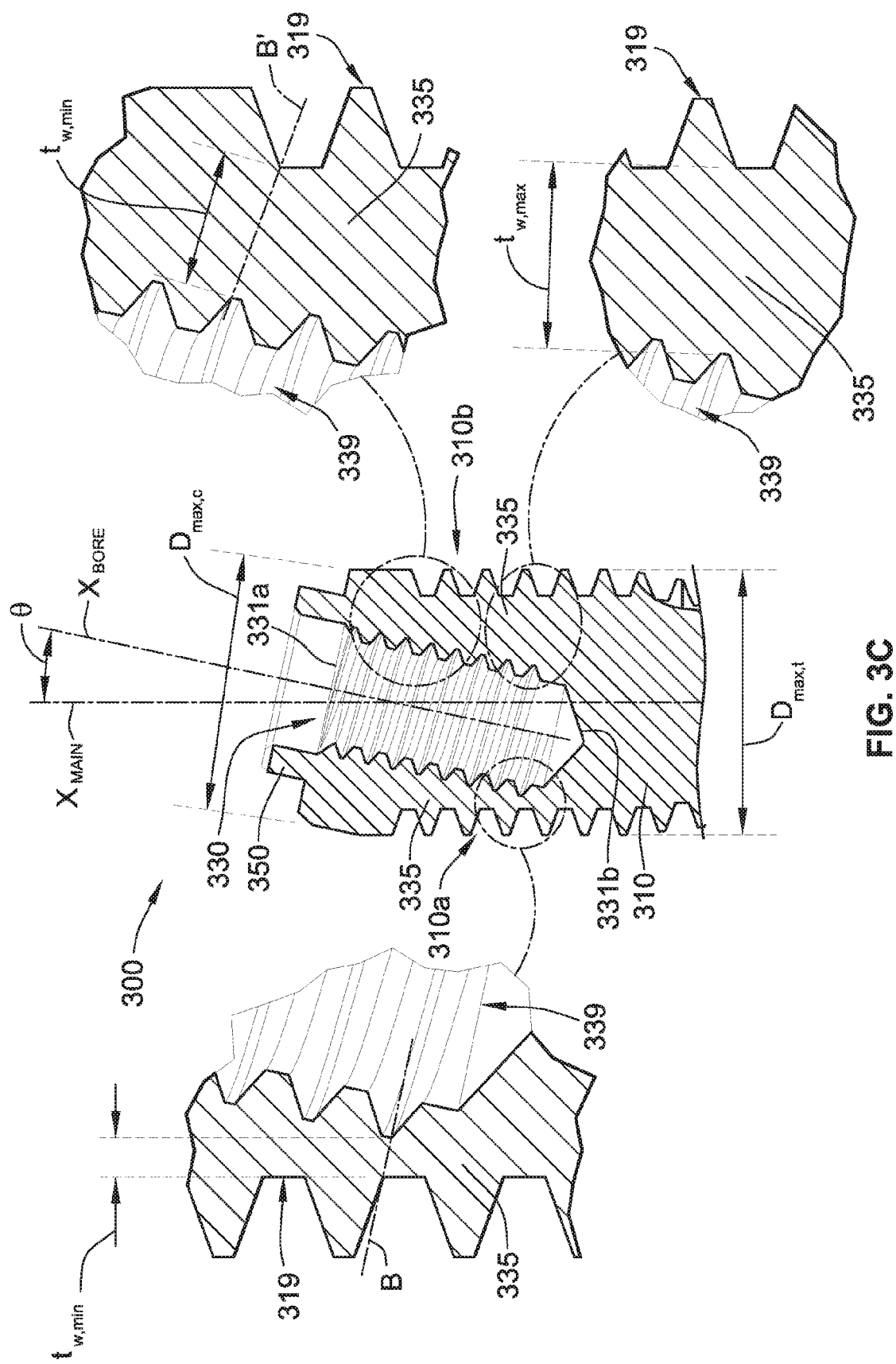
FIG. 3C is a partial cross-sectional view of the dental implant shown in FIG. 3A.

Now referring to FIGS. 3A-3C, an angled dental implant 300 is shown that is similar to the angled dental implant 200 described herein and shown in FIGS. 2A-2C. However, the angled dental implant 300 generally differs from the angled dental implant 200 in that the angled dental implant 300 is generally referred to as a 4.0 millimeter angled dental implant, which is the nominal maximum outer diameter $D_{max,c}$ of a collar section 320 and/or the nominal maximum outer diameter $D_{max,t}$ of a first thread 314a.

The angled dental implant 300 includes a generally cylindrical body 310, an angled portion 313, the collar section 320, an interior bore 330, a non-rotational feature 350, a proximal portion 312a, a distal portion 312b, the first thread 314a, a second thread 314b, flutes 318, a main-central axis $X_{main}$ a bore-central axis $X_{bore}$, and a circumferentially extending wall 335, which are the same as, or similar to, the generally cylindrical body 210, the angled portion 213, the collar section 220, the interior bore 230, the non-rotational feature 250, the proximal portion 212a, the distal portion 212b, the first thread 214a, the second thread 214b, the flutes 218, the main-central axis $X_{main}$ the bore-central axis $X_{bore}$, and the circumferentially extending wall 235 of the angled dental implant 200.

The main difference between the angled dental implants 200 and 300 is the thickness of the circumferentially extending walls 235 and 335, which is caused, at least in part, by the difference between the outer diameters of the angled dental implants 200 and 300. As shown in FIGS. 3A-3C, the circumferentially extending wall 335 is defined by an outer surface 319 of the generally cylindrical body 310 and an inner surface 339 of the interior bore 330. The circumferentially extending wall 335 has a minimum thickness $t_{w,min}$ and a maximum thickness $t_{w,max}$ as best shown in FIG. 3C. The minimum thickness $t_{w,min}$ of the circumferentially extending wall 335 near or at a proximal end 331a of the interior bore 330 is different than the minimum thickness $t_{w,min}$ of the circumferentially extending wall 335 near or at the distal end 331b of the interior bore 330. As an example, the angled dental implant 300 (shown in FIGS. 3A-3C), is a 4.0 diameter angled dental implant (nominal size) with the interior bore 330 having an angle θ of about 12 degrees. In this illustrated example, the minimum thickness $t_{w,min}$ of the circumferentially extending wall 335 at or near the distal end 331b (e.g., taken at line B) of the interior bore 330 is about 0.2 millimeters, which is adjacent to a first side 310a of the generally cylindrical body 310 of the angled dental implant 300. Similarly, the minimum thickness $t_{w,min}$ of the circumferentially extending wall 335 at or near the proximal end 331a (e.g., taken at line B') of the interior bore 330 is about 0.7 millimeters, which is adjacent to a second opposing side 310b of the generally cylindrical body 310 of the angled dental implant 300.

Further, as can be appreciated by the above description and FIGS. 3A-3C, the thickness of the circumferentially extending wall 335 varies about the circumference (e.g., rotational position about the main-central axis $X_{main}$) of the angled dental implant 300 due to the interior bore 330 being at the angle θ relative to the main-central axis $X_{main}$. As best shown in FIG. 3C, for a horizontal cross-section of the generally cylindrical body 310 at or near the distal end 331b of the interior bore 330, the thickness of the circumferentially extending wall 335 varies about the circumference of the angled dental implant 300 from (1) the minimum thickness $t_{w,min}$ at or near the distal end 331b of the interior bore 330 adjacent to the first side 310a to (2) the maximum thickness $t_{w,max}$ at or near the distal end 331b of the interior bore 330 adjacent to the second opposing side 310b.

Based on the exemplary implementation shown in FIGS. 3A-3C of the angled dental implant 300, a ratio of (i) the maximum outer diameter $D_{max,c}$ or $D_{max,t}$ (e.g., the nominal outer diameter of 4.0 millimeters) of the generally cylindrical body 310 to (ii) the thinnest portion (e.g., thickness $t_{w,min}$) of the circumferentially extending wall 335 adjacent to the first side 310a of the generally cylindrical body 310 is 4.0 millimeters/0.2 millimeters, which equals 20.

Figure 4B:
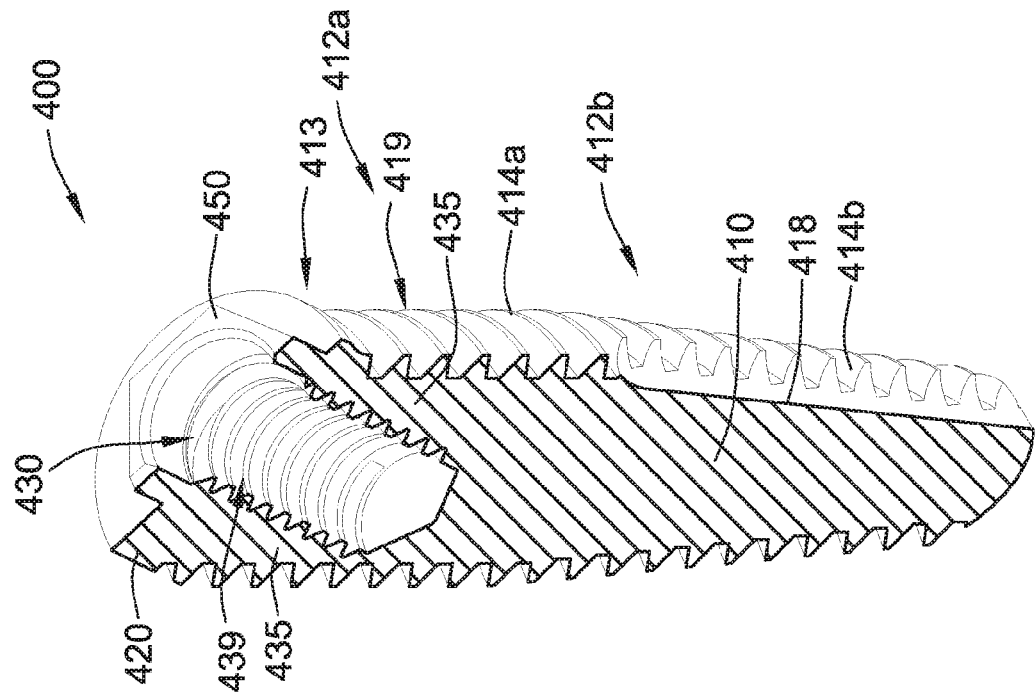
FIG. 4B is a perspective cutaway view of the dental implant shown in FIG. 4A.
Figure 4A:
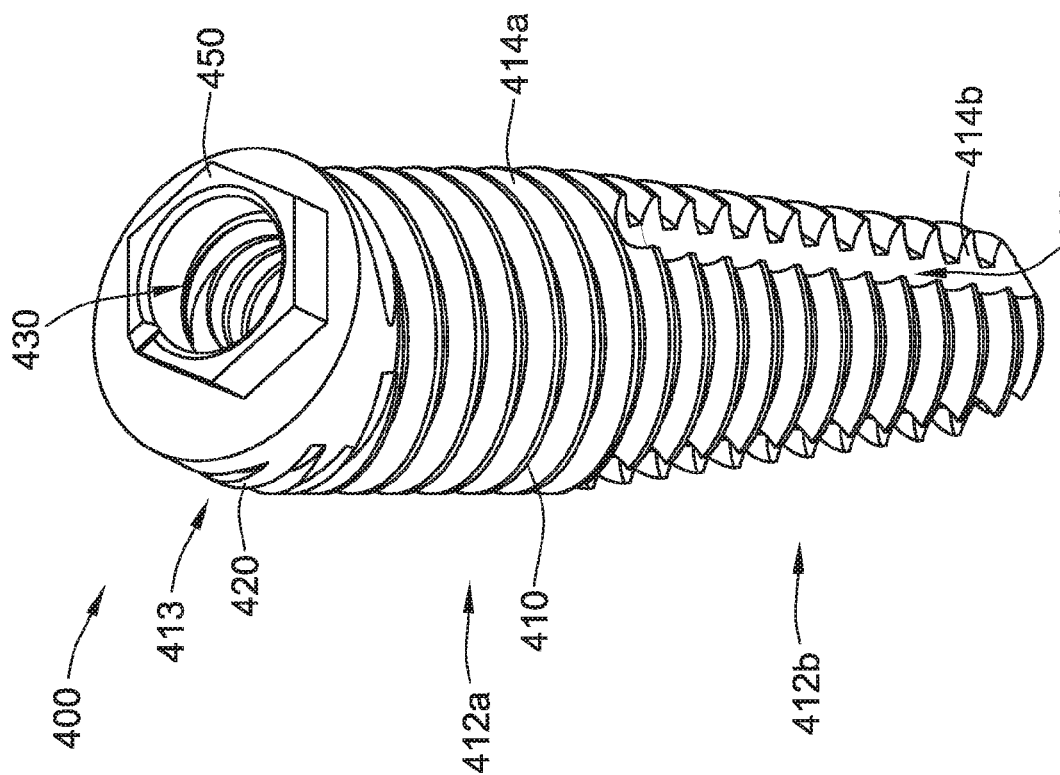
FIG. 4A is a perspective view of an angled-bore dental implant with an external-connection according to some implementations of the present disclosure.
Figure 4C:
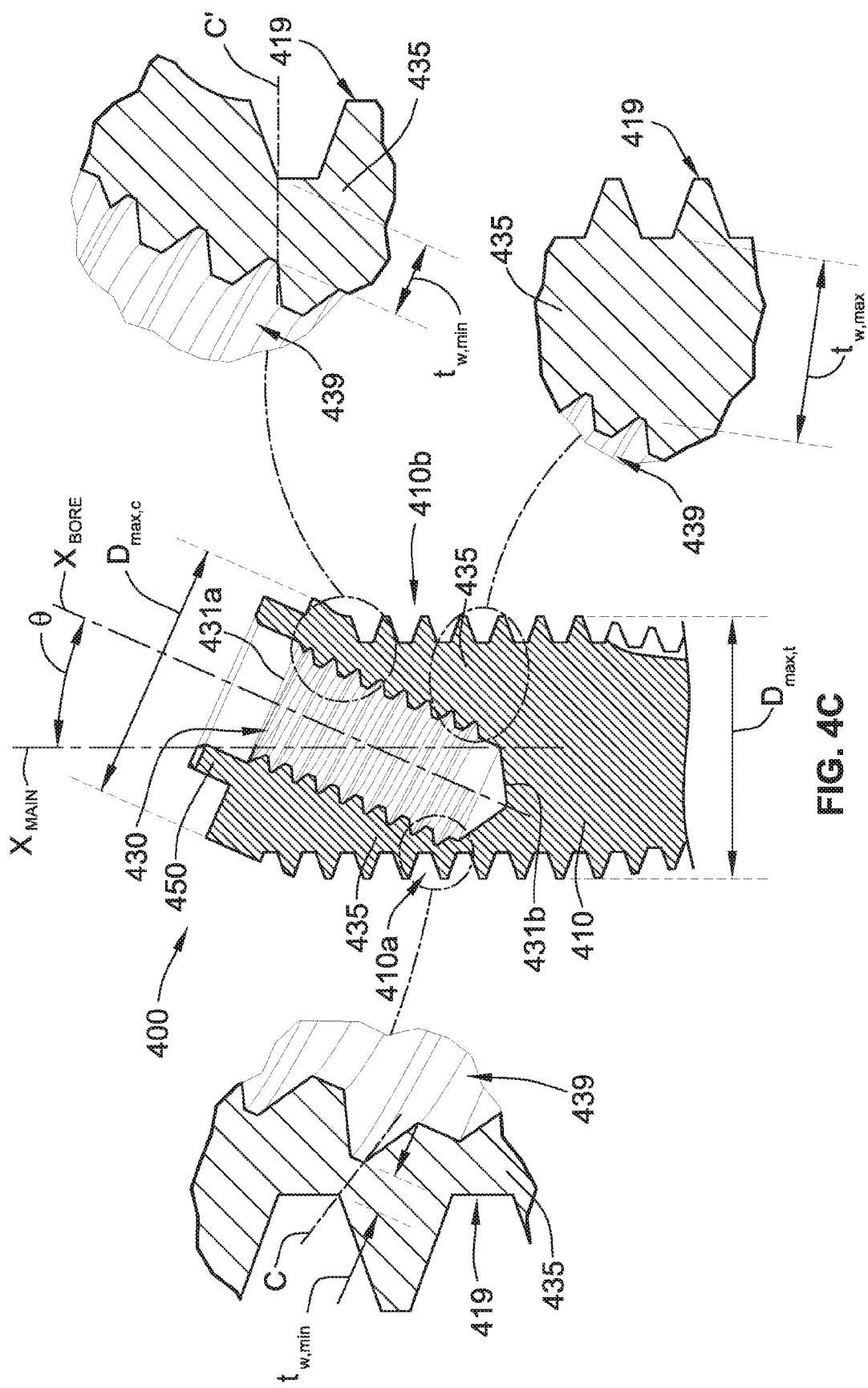
FIG. 4C is a partial cross-sectional view of the dental implant shown in FIG. 4A.

Now referring to FIGS. 4A-4C, an angled dental implant 400 is shown that is similar to the angled dental implant 300 described herein and shown in FIGS. 3A-3C. However, the angled dental implant 400 generally differs from the angled dental implant 300 in that the angled dental implant 400 includes an interior bore 430 with a bore-central axis $X_{bore}$ that is at an angle θ of about 24 degrees relative to a main-central axis $X_{main}$ of the angled dental implant 400, as opposed to the about 12 degree angle of the bore-central axis $X_{bore}$ of the angled dental implant 300 (FIGS. 3A-3C). Further, the angled dental implant 400 is generally referred to as a 4.0 millimeter angled dental implant, which is the nominal maximum outer diameter $D_{max,c}$ of a collar section 420 and/or the nominal maximum outer diameter $D_{max,t}$ of a first thread 414a.

The angled dental implant 400 includes a generally cylindrical body 410, an angled portion 413, the collar section 420, the interior bore 430, a non-rotational feature 450, a proximal portion 412a, a distal portion 412b, the first thread 414a, a second thread 414b, flutes 418, the main-central axis $X_{main}$, the bore-central axis $X_{bore}$, and a circumferentially extending wall 435, which are the same as, or similar to, the generally cylindrical body 310, the angled portion 313, the collar section 320, the interior bore 330, the non-rotational feature 350, the proximal portion 312a, the distal portion 312b, the first thread 314a, the second thread 314b, the flutes 318, the main-central axis $X_{main}$, the bore-central axis $X_{bore}$, and the circumferentially extending wall 335 of the angled dental implant 300.

The main difference between the angled dental implants 300 and 400 is the thickness of the circumferentially extending walls 335 and 435, which is caused, at least in part, by the difference between the angles θ (e.g., about 12 degrees vs. about 24 degrees) of the angled dental implants 300 and 400. As shown in FIGS. 4A-4C, the circumferentially extending wall 435 is defined by an outer surface 419 of the generally cylindrical body 410 and an inner surface 439 of the interior bore 430. The circumferentially extending wall 435 has a minimum thickness $t_{w,min}$ and a maximum thickness $t_{w,max}$ as best shown in FIG. 4C. The minimum thickness $t_{w,min}$ of the circumferentially extending wall 435 near or at a proximal end 431a of the interior bore 430 is different than the minimum thickness $t_{w,min}$ of the circumferentially extending wall 435 near or at the distal end 431b of the interior bore 430. As an example, the angled dental implant 400 (shown in FIGS. 4A-4C), is a 4.0 diameter angled dental implant (nominal size) with the interior bore 430 having an angle θ of about 24 degrees. In this illustrated example, the minimum thickness $t_{w,min}$ of the circumferentially extending wall 435 at or near the distal end 431b (e.g., taken at line C) of the interior bore 430 is about 0.14 millimeters, which is adjacent to a first side 410a of the generally cylindrical body 410 of the angled dental implant 400. Similarly, the minimum thickness $t_{w,min}$ of the circumferentially extending wall 435 at or near the proximal end 431a (e.g., taken at line C') of the interior bore 430 is about 0.4 millimeters, which is adjacent to a second opposing side 410b of the generally cylindrical body 410 of the angled dental implant 400.

Further, as can be appreciated by the above description and FIGS. 4A-4C, the thickness of the circumferentially extending wall 435 varies about the circumference (e.g., rotational position about the main-central axis $X_{main}$) of the angled dental implant 400 due to the interior bore 430 being at the angle θ relative to the main-central axis $X_{main}$. As best shown in FIG. 4C, for a horizontal cross-section of the generally cylindrical body 410 at or near the distal end 431b of the interior bore 430, the thickness of the circumferentially extending wall 435 varies about the circumference of the angled dental implant 400 from (1) a minimum thickness $t_{w,min}$ at or near the distal end 431b of the interior bore 430 adjacent to the first side 410a to (2) the maximum thickness $t_{w,max}$ at or near the distal end 431b of the interior bore 430 adjacent to the second opposing side 410b.

Based on the exemplary implementation shown in FIGS. 4A-4C of the angled dental implant 400, a ratio of (i) the maximum outer diameter $D_{max,c}$ or $D_{max,t}$ (e.g., the nominal outer diameter of 4.0 millimeters) of the generally cylindrical body 410 to (ii) the thinnest portion (e.g., thickness $t_{w,min}$) of the circumferentially extending wall 435 adjacent to the first side 410a of the generally cylindrical body 410 is 4.0 millimeters/0.14 millimeters, which equals 28.6.

Figure 5B:
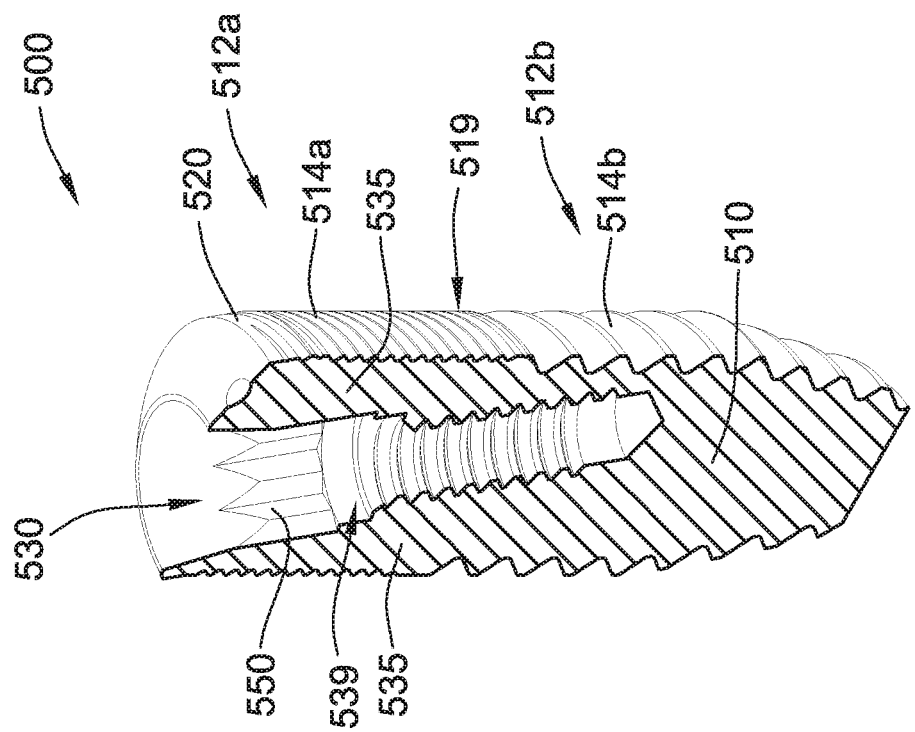
FIG. 5B is a perspective cutaway view of the dental implant shown in FIG. 5A.
Figure 5A:
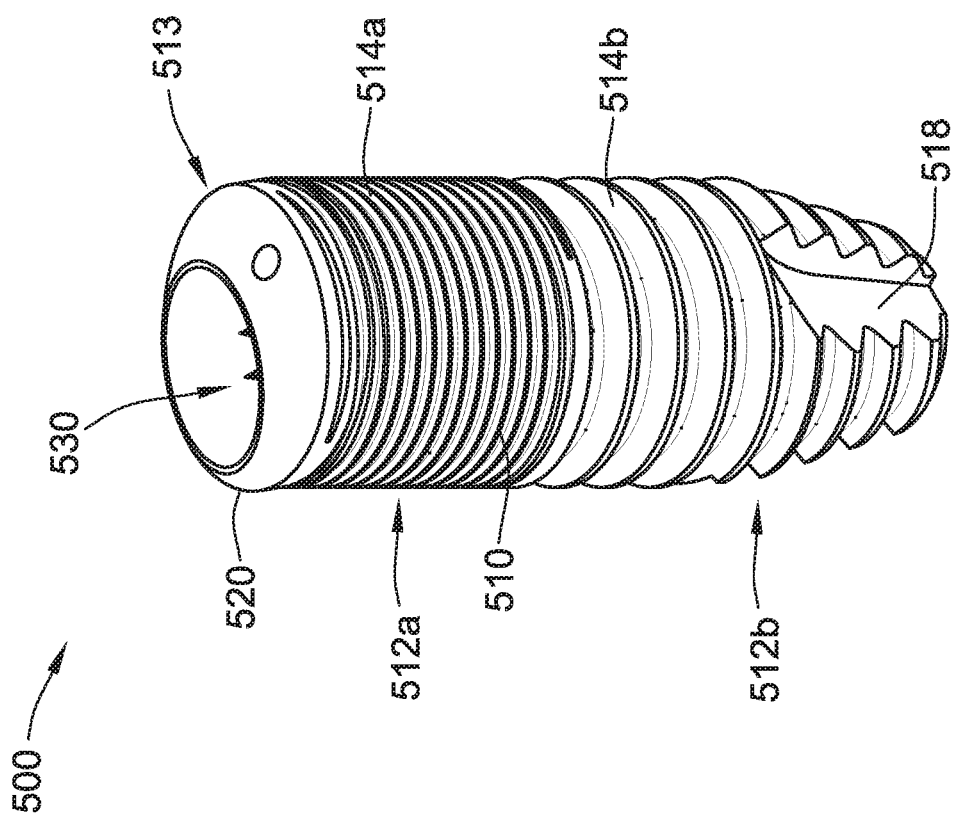
FIG. 5A is a perspective view of an angled-bore dental implant with an internal-connection according to some implementations of the present disclosure.
Figure 5C:
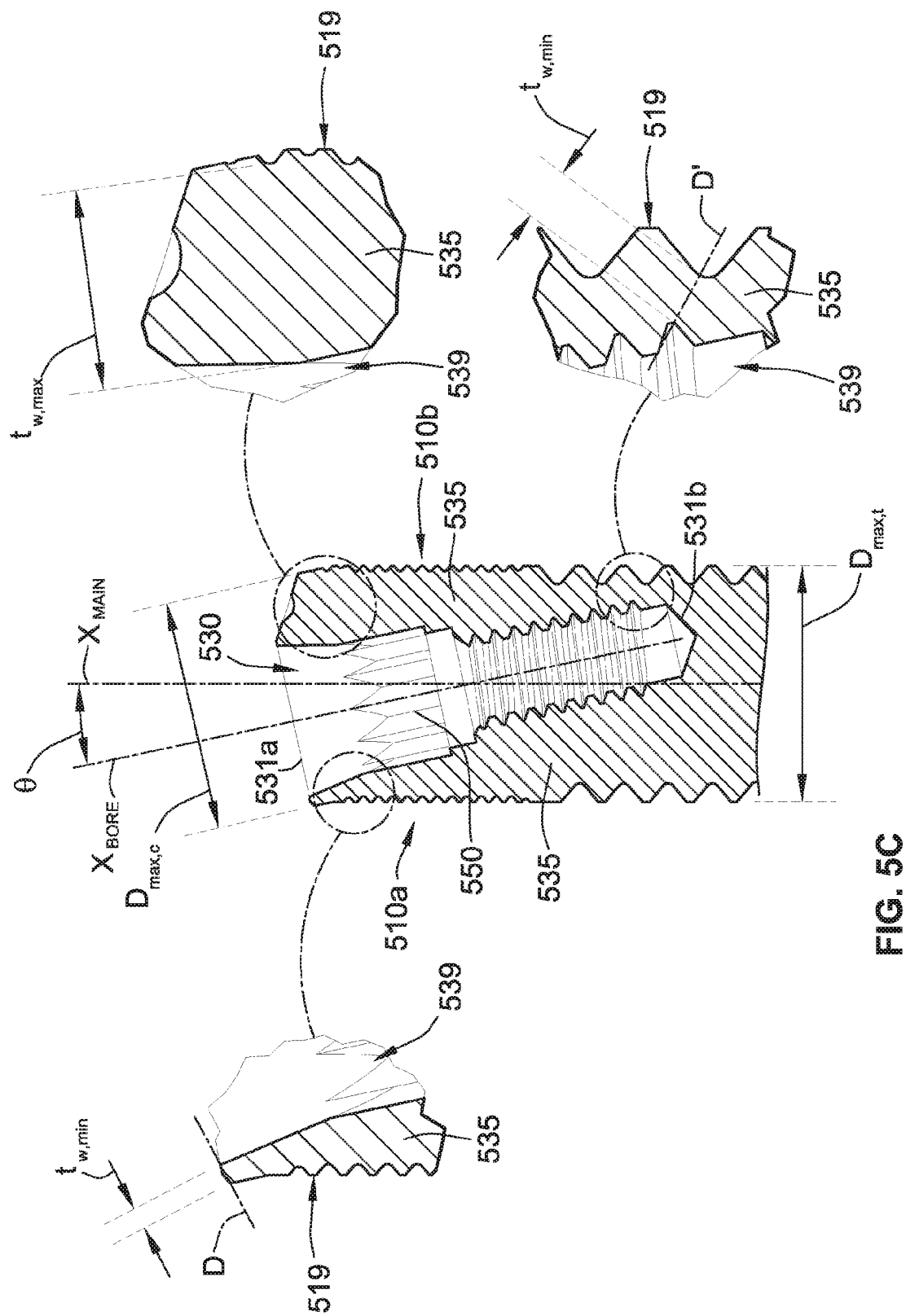
FIG. 5C is a partial cross-sectional view of the dental implant shown in FIG. 5A.

Now referring to FIGS. 5A-5C, an angled dental implant 500 is shown that is similar to the angled dental implants 200, 300, 400 described herein and shown in FIGS. 2A-4C. However, the angled dental implant 500 generally differs from the other angled dental implants 200, 300, 400 in that the angled dental implant 500 is an internal-connection angled dental implant with an internal socket as a non-rotational feature 550 and not an external boss like the non-rotational features 250, 350, 450.

The angled dental implant 500 includes an interior bore 530 with a bore-central axis $X_{bore}$ that is at an angle θ of about 12 degrees relative to a main-central axis $X_{main}$ of the angled dental implant 500. Further, the angled dental implant 500 is generally referred to as a 3.5 millimeter angled dental implant, which is the nominal maximum outer diameter $D_{max,c}$ of a collar section 520 and/or the nominal maximum outer diameter $D_{max,t}$ of a first thread 514a.

The angled dental implant 500 includes a generally cylindrical body 510, an angled portion 513, the collar section 520, the interior bore 530, a proximal portion 512a, a distal portion 512b, the first thread 514a, a second thread 514b, flutes 518, the main-central axis $X_{main}$, the bore-central axis $X_{bore}$, and a circumferentially extending wall 535, which are the same as, or similar to, the generally cylindrical body 210, the angled portion 213, the collar section 220, the interior bore 230, the proximal portion 212a, the distal portion 212b, the first thread 214a, the second thread 214b, the flutes 218, the main-central axis $X_{main}$, the bore-central axis $X_{bore}$, and the circumferentially extending wall 235 of the angled dental implant 200.

The main differences between the angled dental implants 200 and 500 are the non-rotational features 250, 550 and the thickness of the circumferentially extending walls 235 and 535, which is caused, at least in part, by (1) the difference in the non-rotational features 250, 550 and (2) the difference between the outer diameters of the angled dental implants 200 and 500. As shown in FIGS. 5A-5C, the circumferentially extending wall 535 is defined by an outer surface 519 of the generally cylindrical body 510 and an inner surface 539 of the interior bore 530. The circumferentially extending wall 535 has a minimum thickness $t_{w,min}$ and a maximum thickness $t_{w,max}$ as best shown in FIG. 5C. The minimum thickness $t_{w,min}$ of the circumferentially extending wall 535 near or at a proximal end 531a of the interior bore 530 is different than the minimum thickness $t_{w,min}$ of the circumferentially extending wall 535 near or at the distal end 531b of the interior bore 530. As an example, the angled dental implant 500 (shown in FIGS. 5A-5C), is a 3.5 millimeter diameter angled dental implant (nominal size) with the interior bore 530 having an angle θ of about 12 degrees. In this illustrated example, the minimum thickness $t_{w,min}$ of the circumferentially extending wall 535 at or near the proximal end 531a (e.g., taken at line D) of the interior bore 530 is about 0.15 millimeters, which is adjacent to a first side 510a of the generally cylindrical body 510 of the angled dental implant 500. Similarly, the minimum thickness $t_{w,min}$ of the circumferentially extending wall 535 at or near the distal end 531b (e.g., taken at line D') of the interior bore 530 is about 0.32 millimeters, which is adjacent to a second opposing side 510b of the generally cylindrical body 510 of the angled dental implant 500.

Further, as can be appreciated by the above description and FIGS. 5A-5C, the thickness of the circumferentially extending wall 535 varies about the circumference (e.g., rotational position about the main-central axis $X_{main}$) of the angled dental implant 500 due to the interior bore 530 being at the angle θ relative to the main-central axis $X_{main}$. As best shown in FIG. 5C, for a horizontal cross-section of the generally cylindrical body 510 at or near the proximal end 531a of the interior bore 530, the thickness of the circumferentially extending wall 535 varies about the circumference of the angled dental implant 500 from (1) the minimum thickness $t_{w,min}$ at or near the proximal end 531a of the interior bore 530 adjacent to the first side 510a to (2) the maximum thickness $t_{w,max}$ at or near the proximal end 531a of the interior bore 530 adjacent to the second opposing side 510b.

Based on the exemplary implementation shown in FIGS. 5A-5C of the angled dental implant 500, a ratio of (i) the maximum outer diameter $D_{max,c}$ or $D_{max,t}$ (e.g., the nominal outer diameter of 3.5 millimeters) of the generally cylindrical body 510 to (ii) the thinnest portion (e.g., thickness $t_{w,min}$) of the circumferentially extending wall 535 adjacent to the first side 510a of the generally cylindrical body 510 is 3.5 millimeters/0.15 millimeters, which equals 23.3.

Figure 6B:
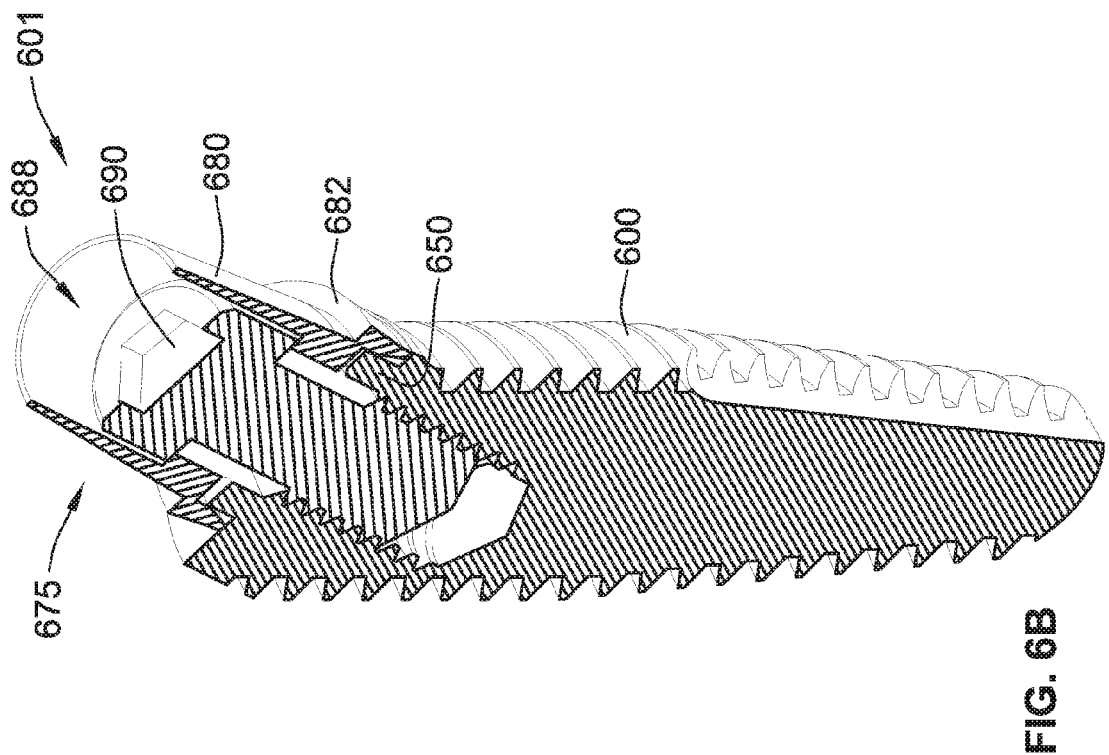
FIG. 6B is an assembled perspective cutaway view of the dental assembly shown in FIG. 6A.
Figure 6A:
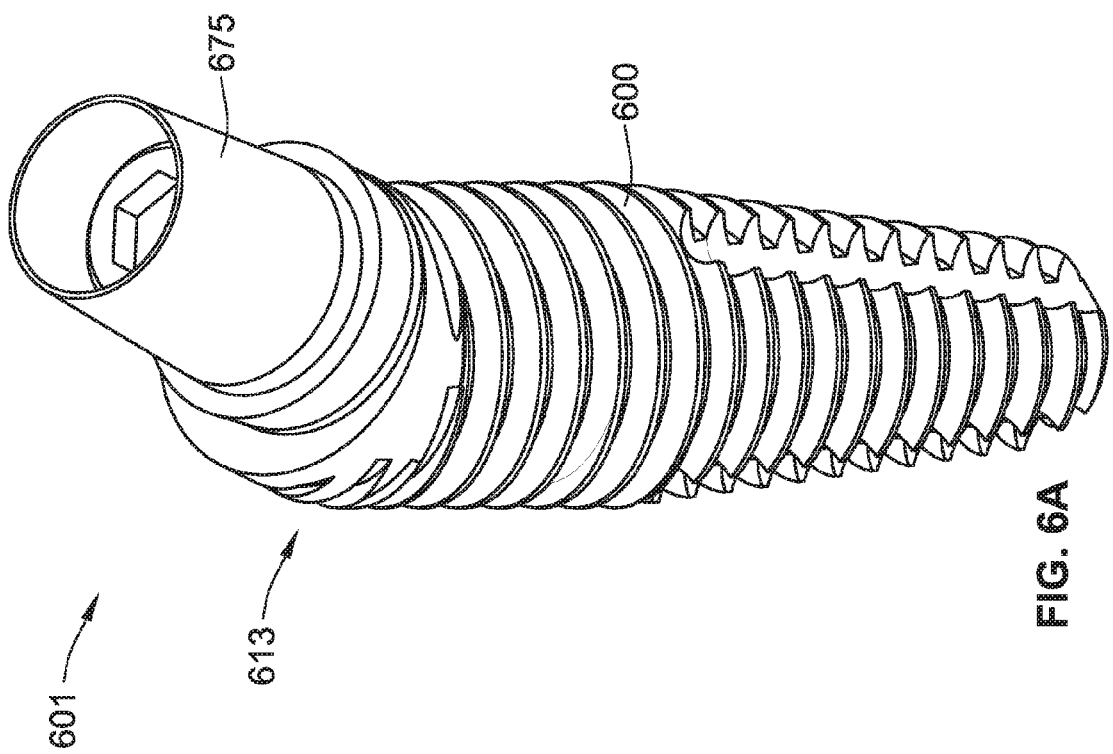
FIG. 6A is an assembled perspective view of a dental assembly including an abutment, a screw, and an angled-bore dental implant with an external-connection according to some implementations of the present disclosure.
Figure 6C:
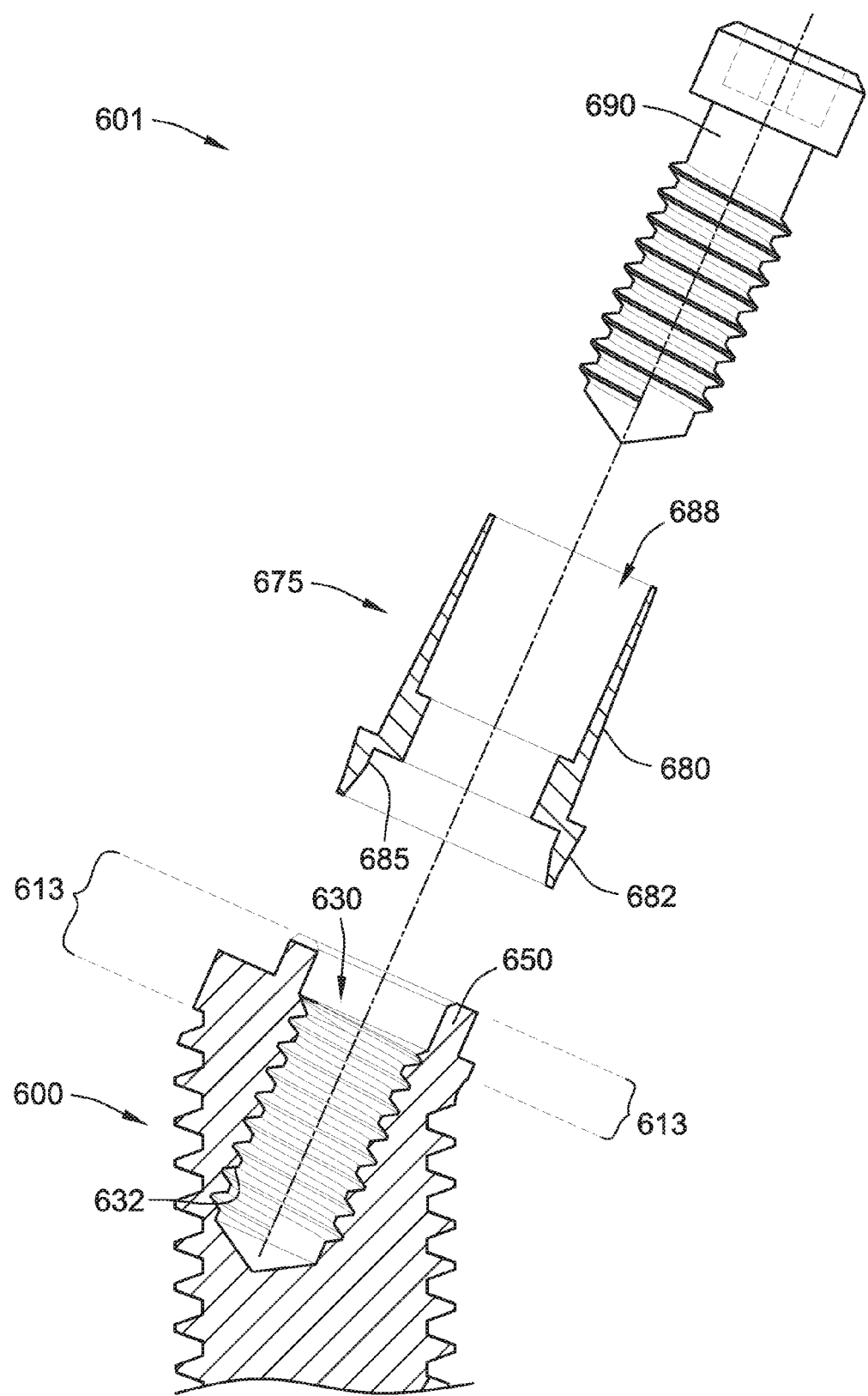
FIG. 6C is an exploded partial cross-sectional view of the dental assembly shown in FIG. 6A.

Now referring to FIGS. 6A-6C, a dental assembly 601 includes an angled dental implant 600, an abutment 675, and a screw 690. The angled dental implant 600 is the same as, or similar to, the angled dental implants 200, 300, 400, 500 described herein.

The abutment 675 includes a post 680 and a stem 682 extending in a relative downward direction from the post 680. The post 680 is sized and shaped to support a restoration thereon (e.g., a crown). The stem 682 may include a non-rotational feature 685 for engaging a non-rotational feature 650 of the angled dental implant 600 in a non-rotational fashion such that the abutment 675 is prevented from rotating relative to the angled dental implant 600 when coupled thereto (e.g., by the screw 690).

The abutment 675 includes a through-bore 688 that extends through the post 680 and the stem 682 to allow the screw 690 to be inserted therein. The screw 690 is inserted into the through-bore 688 of the abutment 675 to threadably engage female or internal threads 632 of an interior bore 630 of the angled dental implant 600 as best shown in FIG. 6B.

Due to the angled dental implant 600 having an angled portion 613, the post 680 of the abutment 675 does not need to be angled relative to the base 678 of the abutment 675 to provide an anatomical tooth restoration.

Figure 7A:
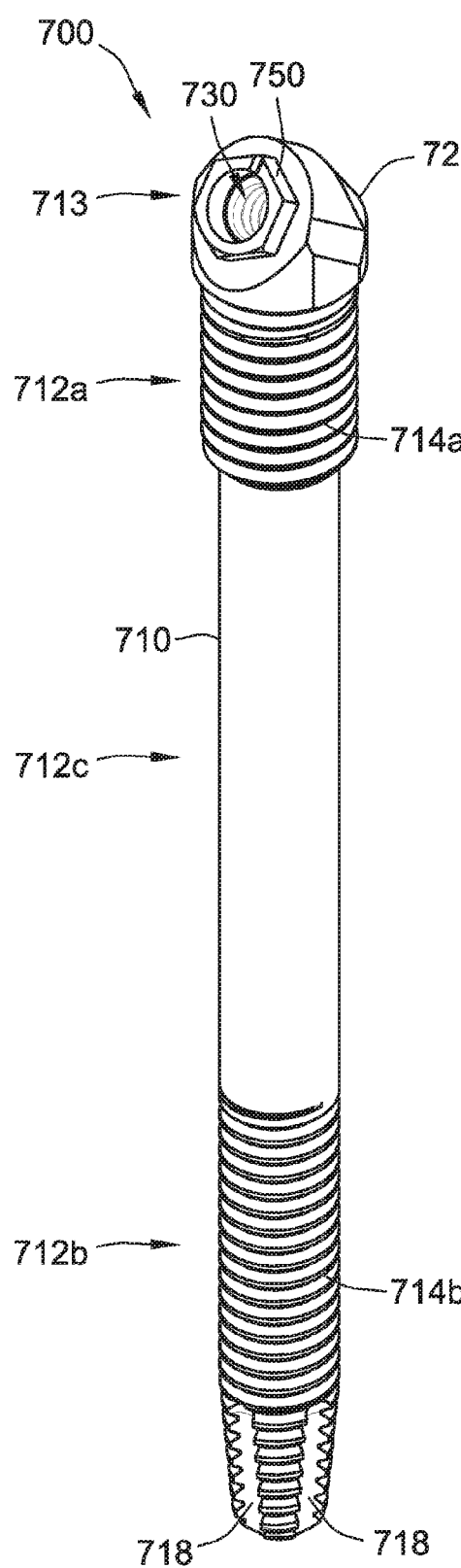
FIG. 7A is a perspective view of an angled-bore zygomatic dental implant with an external-connection according to some implementations of the present disclosure.
Figure 7B:
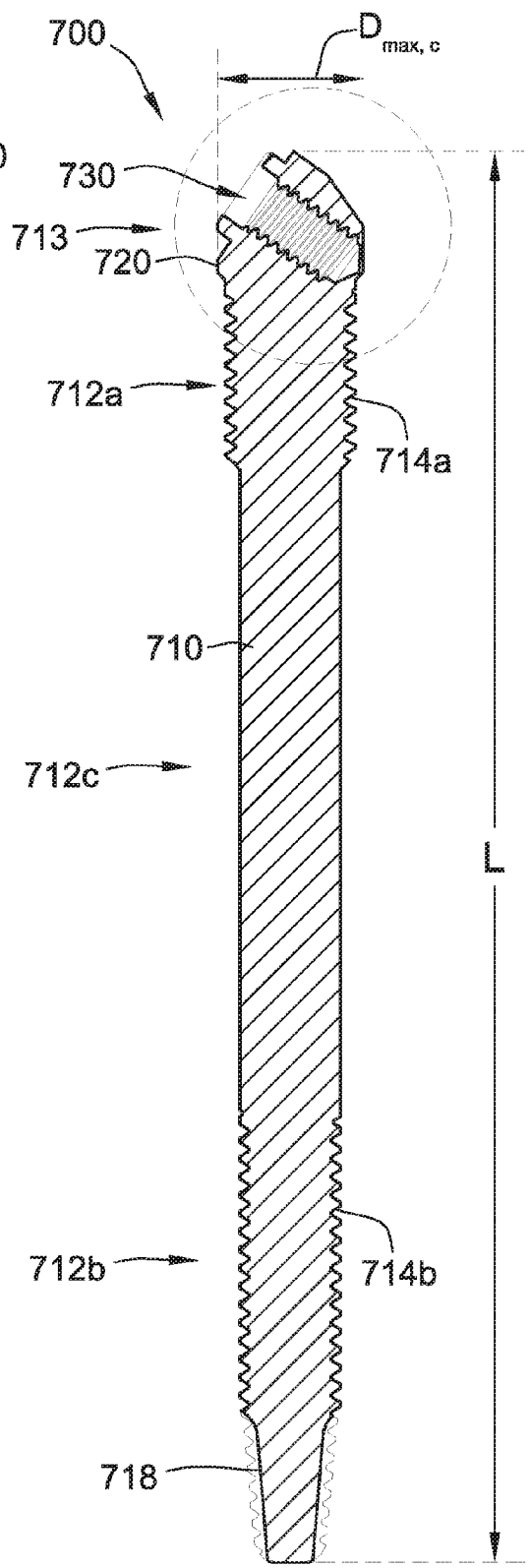
FIG. 7B is a perspective cutaway view of the zygomatic dental implant shown in FIG. 7A.
Figure 7C:
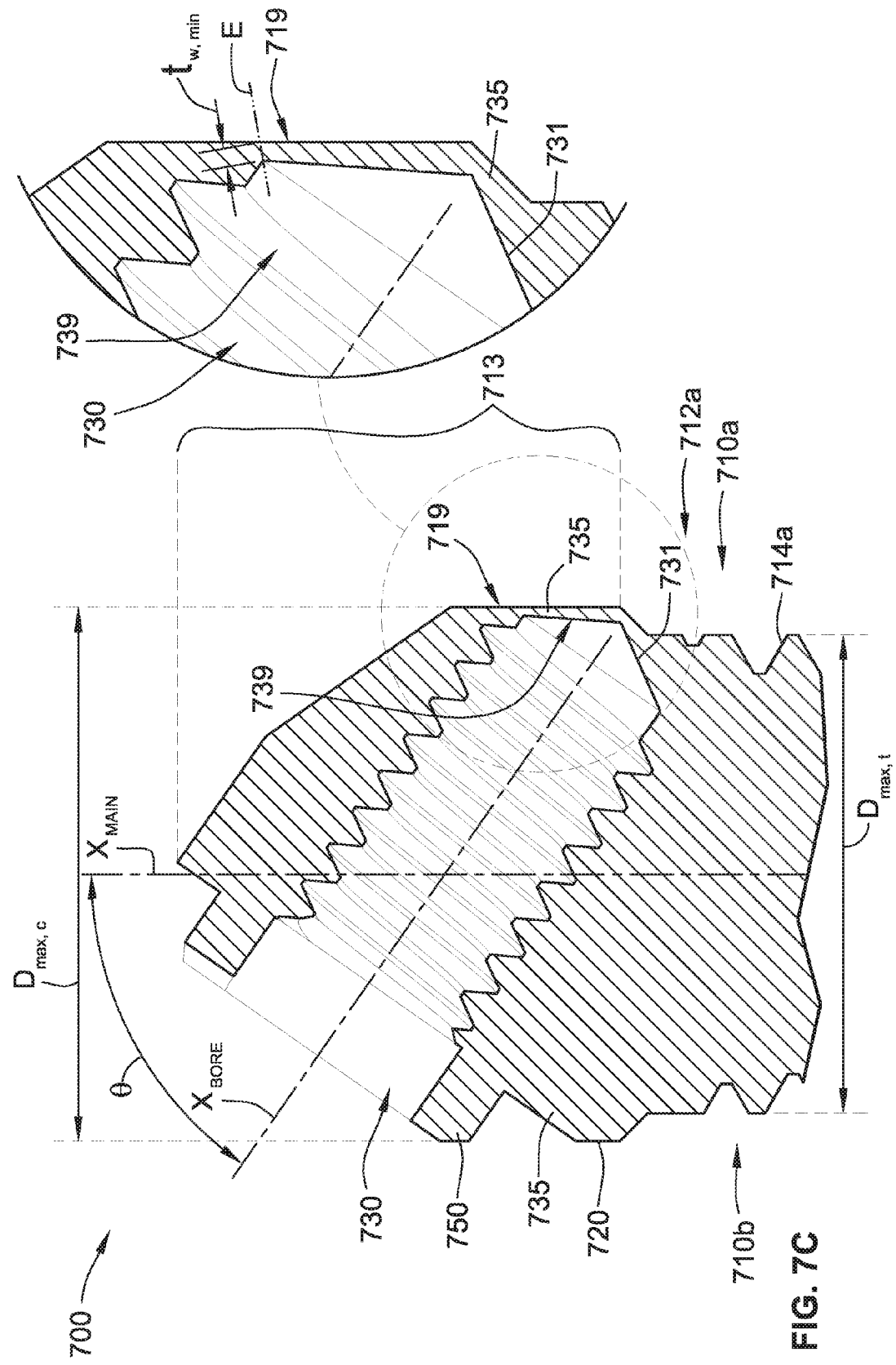
FIG. 7C is a partial cross-sectional view of the zygomatic dental implant shown in FIG. 7A.

Now referring to FIGS. 7A-7C, an angled dental implant 700 is shown that is similar to the angled dental implant 200 described herein and shown in FIGS. 2A-2C. However, the angled dental implant 700 generally differs from the angled dental implant 200 in that the angled dental implant 700 is an angled zygomatic dental implant that is significantly longer than non-zygomatic angled dental implants (e.g., dental implants 200, 300, 400, 500) such that the angled zygomatic dental implant 700 can be installed into a patient's upper jawbone close to the zygoma bone in the patient's mouth. Zygomatic dental implants may be necessary for patients with resorbed and/or deteriorated jaw bones (e.g., cancer patients) that do not provide the necessary socket for installing a non-zygomatic or more traditional dental implant (e.g., dental implants 200, 300, 400, 500). In some implementations, one or more zygomatic dental implants are installed in a patient's mouth (with or without one or more non-zygomatic dental implants) and coupled to one or more abutments, bridges, bars, prosthetic teeth, attachment members, or any combination thereof (e.g., a bridge including prosthetic teeth).

The angled zygomatic dental implant 700 is generally referred to as a 4.5 millimeter zygomatic angled dental implant, where 4.5 millimeters is the nominal maximum outer diameter $D_{max,c}$ of a collar section 720 and/or the nominal maximum outer diameter $D_{max,t}$ of a first thread 714a, and where zygomatic indicates the dental implant 700 has a length L between about 20 millimeters and about 70 millimeters, more specifically, zygomatic can indicate the dental implant 700 has a length L between about 25 millimeters and about 60 millimeters. In some implementations, zygomatic indicates the dental implant 700 has a length of about 25 millimeters, about 30 millimeters, about 35 millimeters, about 40 millimeters, about 45 millimeters, about 50 millimeters, about 55 millimeters, about 60 millimeters, about 65 millimeters, about 70 millimeters. Such a length L of the angled zygomatic dental implant 700 is significantly longer than non-zygomatic angled dental implants (e.g., angled dental implants 200, 300, 400, 500), which typically have a length between about 7 millimeters and about 18 millimeters, more specifically, non-zygomatic angled dental implants have a length between about 8 millimeters and about 15 millimeters.

The angled zygomatic dental implant 700 further differs from the angled dental implant 200 in that the angled zygomatic dental implant 700 includes a non-threaded middle portion 712c of a generally cylindrical body 710 between a proximal portion 712a of the generally cylindrical body 710 and a distal portion 712b of the generally cylindrical body 710. The non-threaded middle portion 712c has a length that is between about 20 percent and about 70 percent of a total length of the angled zygomatic dental implant 700, more preferably, the non-threaded middle portion 712c has a length that is between about 35 percent and about 55 percent of a total length of the angled zygomatic dental implant 700. In some implementations, the non-threaded middle portion 712c has a length that is about 45 percent of a total length of the angled zygomatic dental implant 700.

The angled zygomatic dental implant 700 further differs from the angled dental implant 200 in that the angled zygomatic dental implant 700 has a bore-central axis $X_{bore}$ of the interior bore 730 that is at an angle θ relative to a main-central axis $X_{main}$ of the angled zygomatic dental implant 700, where the angle θ can be any angle, such as, for example, between about 7° and about 65°, or between about 40° and about 65°. As shown in FIGS. 7A-7C, the angle θ is about 55°.

The angled zygomatic dental implant 700 includes the generally cylindrical body 710, an angled portion 713, a collar section 720, an interior bore 730, a non-rotational feature 750, the proximal portion 712a, the distal portion 712b, the first thread 714a, a second thread 714b, flutes 718, a main-central axis $X_{main}$, a bore-central axis $X_{bore}$, and a circumferentially extending wall 735, which are the same as, or similar to, the generally cylindrical body 210, the angled portion 213, the collar section 220, the interior bore 230, the non-rotational feature 250, the proximal portion 212a, the distal portion 212b, the first thread 214a, the second thread 214b, the flutes 218, the main-central axis $X_{main}$, the bore-central axis $X_{bore}$, and the circumferentially extending wall 235 of the angled dental implant 200.

As shown in FIGS. 7A-7C, the circumferentially extending wall 735 is defined by an outer surface 719 of the generally cylindrical body 710 and an inner surface 739 of the interior bore 730. The circumferentially extending wall 735 has a minimum thickness $t_{w,min}$ as best shown in FIG. 7C. The minimum thickness $t_{w,min}$ of the circumferentially extending wall 735 is near or at a distal end 731 of the interior bore 730. As an example, the angled zygomatic dental implant 700 (shown in FIGS. 7A-7C), is a 4.5 diameter angled zygomatic dental implant (nominal size) with the interior bore 730 having an angle θ of about 55 degrees. In this illustrated example, the minimum thickness $t_{w,min}$ of the circumferentially extending wall 735 at or near the distal end 731 (e.g., taken at line E) of the interior bore 730 is about 0.08 millimeters, which is adjacent to a first side 710a of the generally cylindrical body 710 of the angled dental implant 700.

Further, as can be appreciated by the above description and FIGS. 7A-7C, the thickness of the circumferentially extending wall 735 varies about the circumference (e.g., rotational position about the main-central axis $X_{main}$) of the angled zygomatic dental implant 700 due to the interior bore 730 being at the angle θ relative to the main-central axis $X_{main}$. As best shown in FIG. 7C, for a horizontal cross-section of the generally cylindrical body 710 at or near the distal end 731 of the interior bore 730, the thickness of the circumferentially extending wall 735 varies about the circumference of the angled dental implant 700 from (1) the minimum thickness $t_{w,min}$ at or near the distal end 731 of the interior bore 730 adjacent to the first side 710a to (2) a relatively larger and/or maximum thickness at or near the distal end 731 of the interior bore 730 adjacent to a second opposing side 710b.

Based on the exemplary implementation shown in FIGS. 7A-7C of the angled zygomatic dental implant 700, a ratio of (i) the maximum outer diameter $D_{max,c}$ or $D_{max,t}$ (e.g., the nominal outer diameter of 4.5 millimeters) of the generally cylindrical body 710 to (ii) the thinnest portion (e.g., thickness $t_{w,min}$) of the circumferentially extending wall 735 adjacent to the first side 710a of the generally cylindrical body 710 is 4.5 millimeters/0.08 millimeters, which equals 56.25.

The proximal portion 712a of the generally cylindrical body 710 has a relatively larger maximum outer diameter than the maximum outer diameter of the non-threaded middle portion 712c of the generally cylindrical body 710 and the maximum outer diameter of the distal portion 712b of the generally cylindrical body 710. For example, as shown, (i) the maximum outer diameter of the threaded proximal portion 712a is about 4.3 millimeters and (ii) the maximum outer diameter of the threaded distal portion 712b and the maximum outer diameter of the non-threaded middle portion 712c is between about 3.2 millimeters and about 4 millimeters. Alternatively, the maximum outer diameter of the threaded distal portion 712b and the maximum outer diameter of the non-threaded middle portion 712c are the same as, or about the same as, the maximum outer diameter of the threaded proximal portion 712a.

Figure 8:
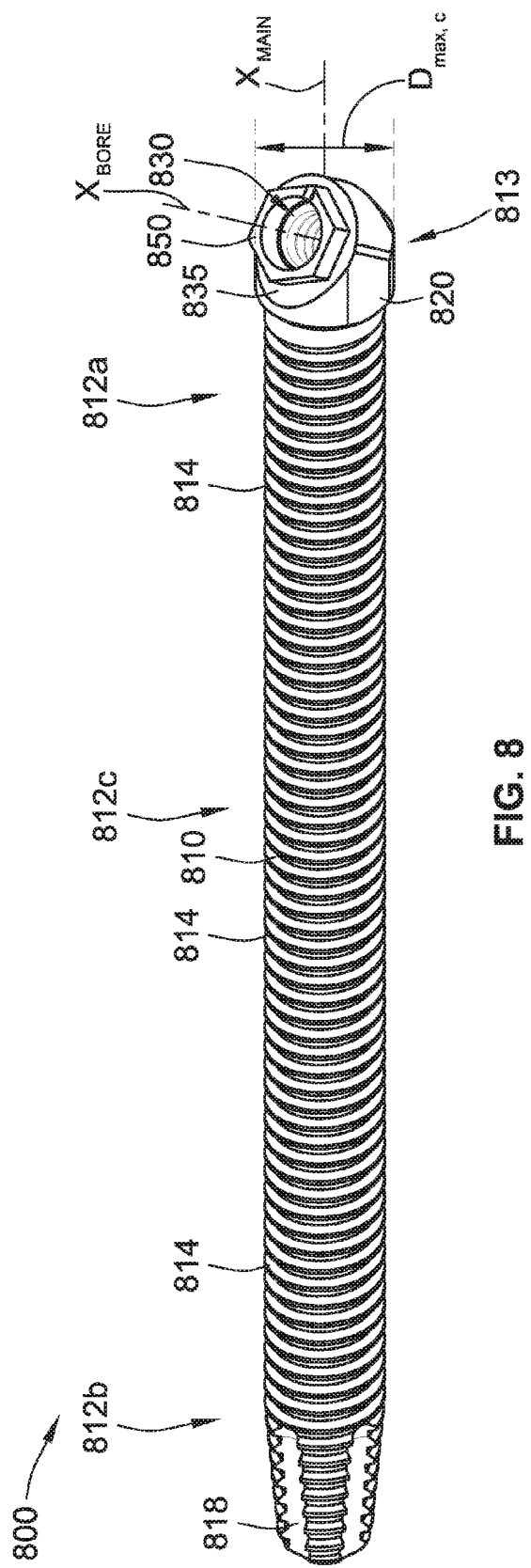
FIG. 8 is a perspective view of an angled-bore zygomatic dental implant with an external-connection according to some implementations of the present disclosure.

Now referring to FIG. 8, an angled zygomatic dental implant 800 is shown that is similar to the angled zygomatic dental implant 700 described herein and shown in FIGS. 7A-7C. However, the angled zygomatic dental implant 800 generally differs from the angled zygomatic dental implant 700 in that the angled zygomatic dental implant 800 lacks a non-threaded middle portion. Rather, the angled zygomatic dental implant 800 includes a generally cylindrical body 810 that has a proximal or upper threaded portion 812a of the generally cylindrical body 810, a distal or lower threaded portion 812b of the generally cylindrical body 810, and a middle threaded portion 812c of the generally cylindrical body 810, where a single constant thread 814 is wrapped around the distal, middle, and proximal portions 812a,b,c. Alternatively, the thread 814 can vary along the length of the generally cylindrical body 810 (e.g., vary in pitch, depth, etc.).

The angled zygomatic dental implant 800 is generally referred to as a 3.5 millimeter zygomatic angled dental implant, where 3.5 millimeters is the nominal maximum outer diameter $D_{max,c}$ of a collar section 820 and/or the nominal maximum outer diameter $D_{max,t}$ of the thread 814. The angled zygomatic dental implant 800 includes the generally cylindrical body 810, an angled portion 813, the collar section 820, an interior bore 830, a non-rotational feature 850, the proximal portion 812*a*, the distal portion 812*b*, flutes 818, a main-central axis $X_{main}$, a bore-central axis $X_{bore}$, and a circumferentially extending wall 835, which are the same as, or similar to, the generally cylindrical body 710, the angled portion 713, the collar section 720, the interior bore 730, the non-rotational feature 750, the proximal portion 712*a*, the distal portion 712*b*, the flutes 718, the main-central axis $X_{main}$, the bore-central axis $X_{bore}$, and the circumferentially extending wall 735 of the angled zygomatic dental implant 700.

Figure 9:
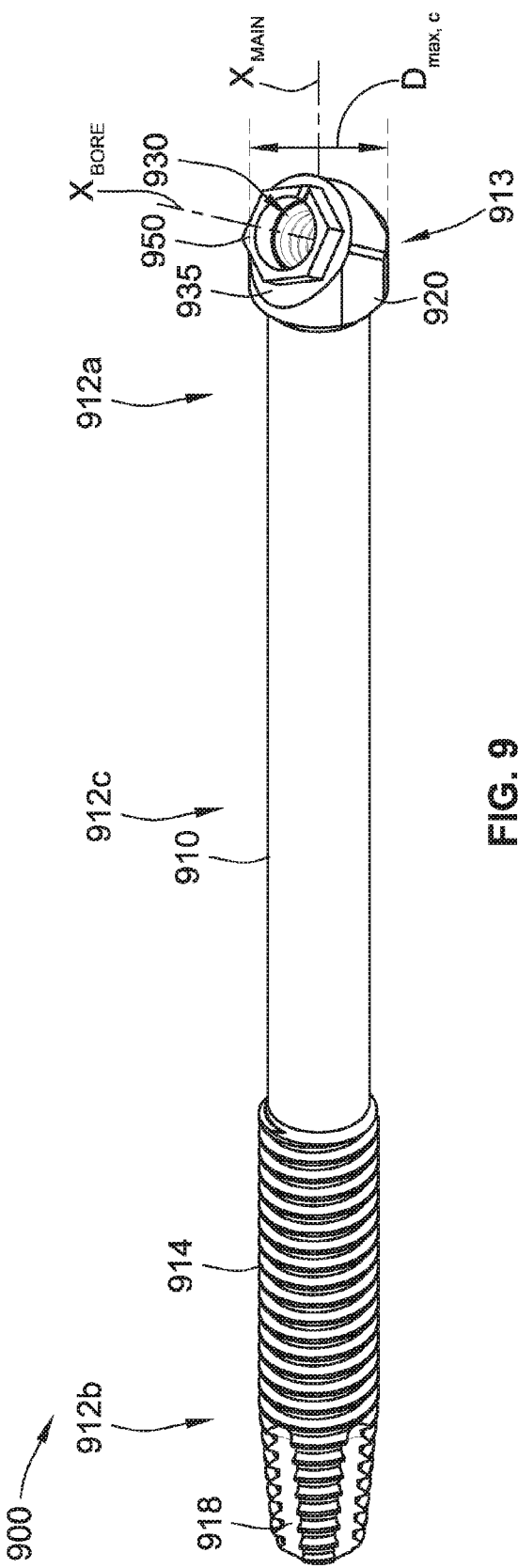
FIG. 9 is a perspective view of an angled-bore zygomatic dental implant with an external-connection according to some implementations of the present disclosure.

Now referring to FIG. 9, an angled zygomatic dental implant 900 is shown that is similar to the angled zygomatic dental implants 700, 800 described herein and shown in FIGS. 7A-8. However, the angled zygomatic dental implant 900 generally differs from the angled zygomatic dental implants 700, 800 in that the angled zygomatic dental implant 900 lacks a threaded proximal portion. Rather, the angled zygomatic dental implant 900 includes a generally cylindrical body 910 that has a proximal or upper non-threaded portion 912*a* of the generally cylindrical body 910, a middle non-threaded portion 912*c* of the generally cylindrical body 910, and a distal or lower threaded portion 912*b* of the generally cylindrical body 910.

A single constant thread 914 is wrapped around the distal portion 912*b*. As shown, a maximum outer diameter of the proximal and middle portions 912*a,c* is equal or about equal to a minor diameter of the threaded distal portion 912*b*. Alternatively, the maximum outer diameter of the proximal and middle portions 912*a,c* is equal or about equal to a major diameter of the threaded distal portion 912*b*.

A combined length of the non-threaded proximal and middle portions 912*a,c* is between about 20 percent and about 85 percent of a total length of the angled zygomatic dental implant 900, more preferably, the combined length of the non-threaded proximal and middle portions 912*a,c* is between about 35 percent and about 70 percent of a total length of the angled zygomatic dental implant 900. In some implementations, the combined length of the non-threaded proximal and middle portions 912*a,c* is about 60 percent of a total length of the angled zygomatic dental implant 900. In some implementations, the combined length of the non-threaded proximal and middle portions 912*a,c* is about 30 percent of a total length of the angled zygomatic dental implant 900.

The angled zygomatic dental implant 900 is generally referred to as a 3.5 millimeter zygomatic angled dental implant, where 3.5 millimeters is the nominal maximum outer diameter $D_{max,c}$ of a collar section 920. The angled zygomatic dental implant 900 includes the generally cylindrical body 910, an angled portion 913, the collar section 920, an interior bore 930, a non-rotational feature 950, the middle portion 912*c*, the distal portion 912*b*, flutes 918, a main-central axis $X_{main}$, a bore-central axis $X_{bore}$, and a circumferentially extending wall 935, which are the same as, or similar to, the generally cylindrical body 710, the angled portion 713, the collar section 720, the interior bore 730, the non-rotational feature 750, the middle portion 712*c*, the distal portion 712*b*, the flutes 718, the main-central axis $X_{main}$, the bore-central axis $X_{bore}$, and the circumferentially extending wall 735 of the angled zygomatic dental implant 700.

Various dental implants are described herein and shown in the FIGS. as having certain maximum outer diameters (e.g., nominal size of the dental implants), certain lengths, certain threaded portions, certain non-threaded portions, certain connection types, and interior bores with certain angles, which all can contribute to the various dental implants of the present disclosure having a measurable thinnest portion of its circumferentially extending wall (e.g., circumferentially extending wall 235). The following table provides examples of dental implants (e.g., straight dental implants, angled dental implants, zygomatic dental implants) along with their thinnest portion of the wall and the ratio of the maximum outer diameter (e.g., nominal size) to the thinnest portion of the wall of the dental implant.

TABLE 1

| Max Outer Diameter of Implant (OD max) | Connection Type | Angle of Interior Bore (degrees) | Thinnest Portion of Wall (TPW) (mm) | Ratio (OD max/TPW) |
|---|---|---|---|---|
| 3.25 | External | 12 | 0.04 | 81.3 |
| 3.8 | External | 55 | 0.06 | 63.3 |
| 4.8 | External | 55 | 0.08 | 60.0 |
| 3.5 | External | 55 | 0.06 | 58.3 |
| 4.50 | External | 55 | 0.08 | 56.25 |
| 4.00 | External | 24 | 0.14 | 28.6 |
| 3.50 | Internal | 12 | 0.15 | 23.3 |
| 4.00 | External | 12 | 0.2 | 20.0 |
| 4.00 | Internal | 12 | 0.25 | 16.0 |
| 3.52 | Internal | 0 | 0.35 | 10.1 |
| 3.00 | Internal | 0 | 0.35 | 8.6 |
| 5.00 | Internal | 0 | 0.6 | 8.3 |
| 3.25 | External | 0 | 0.47 | 6.9 |
| 4.00 | Internal | 0 | 0.6 | 6.7 |

While the dental implants of the present disclosure are described as being machined from cold-worked, high strength, commercially pure (e.g., Grade IV) titanium, in some alternative implementations, the dental implants of the present disclosure can be machined from one or more titanium alloys, such as, for example, an alloy of titanium and one or more of the following materials: Vanadium, Aluminium, Niobium, Zirconium, Chromium, or any combination thereof. In some alternative implementations, the dental implants of the present disclosure are machined from a titanium alloy that includes about 90% Titanium, about 6% Aluminium, and about 4% Vanadium. In some other alternative implementations, the dental implants of the present disclosure are machined from a titanium alloy that includes about 86% Titanium and about 14% Zirconium. In yet some other alternative implementations, the dental implants of the present disclosure are machined from a titanium alloy that includes about 83% Titanium and about 17% Zirconium. In such implementations using one of the described a Titanium-Zirconium alloys, the Titanium-Zirconium alloy material has an ultimate tensile strength of about 950 MPa. In some other alternative implementations, the dental implants of the present disclosure are machined from a titanium alloy that includes about 98% Titanium and about 2% Niobium. In yet some other alternative implementations, the dental implants of the present disclosure are machined from a titanium alloy that includes about 87% Titanium, about 6% Aluminium, and about 7% Niobium. In some other alternative implementations, the dental implants of the present disclosure are machined from a titanium alloy that includes about 91% Titanium, about 6% Aluminium, and about 3% Niobium. In some other alternative implementations, the dental implants of the present disclosure are machined from a titanium alloy that includes about 77% Titanium, about 3% Aluminium, about 9% Niobium, and about 11% Chromium.

The dental implants of the present disclosure are shown and described as including a first thread (e.g., 114a, 214a, 314a, 414a, 514a) and a second thread (e.g., 114b, 214b, 314b, 414b, 514b). For example, the angled dental implant 500 includes the first thread 514a and the second thread 514b. The first thread 514a is also known as a micro thread (about the distal portion 512b) and the second thread 514b is also known as is a main thread 514b (about the proximal portion 512b). By micro thread, it is meant that the micro thread 514a has a relatively smaller peak-to-trough distance as compared with the main thread 514b. By having the first thread 514a be a micro thread 514a (as opposed to just being a continuation of the second thread 514b with the same major thread diameter, the same minor thread diameter, etc.) the minor thread diameter of the micro thread 514a is relatively larger than the minor thread diameter of the main thread 514b. As such, the circumferentially extending wall 535 is relatively thicker than it would have been if the minor thread diameter of the first thread 514a was equal to the minor thread diameter of the second thread 514b. As such, with the circumferentially extending wall 535 being relatively thicker, the angled dental implant 500 is relatively stronger.

Some of the dental implants of the present disclosure are shown and described as being machined from cold-worked, high strength, commercially pure (e.g., Grade IV) titanium. In some such implementations, these dental implants machined from cold-worked, high strength, commercially pure (e.g., Grade IV) titanium have a fatigue strength of at least about 200 newtons, at least about 225 newtons, or at least about 250 newtons.

While the present disclosure has been described with reference to one or more particular embodiments and implementations, those skilled in the art will recognize that many changes may be made thereto without departing from the spirit and scope of the present disclosure. Each of these embodiments and implementations and obvious variations thereof is contemplated as falling within the spirit and scope of the present disclosure, which is set forth in the claims that follow.

What is claimed is:

1. An angled dental implant, comprising:
 a generally cylindrical body having a maximum outer diameter and a main-central axis, the generally cylindrical body being formed from cold-worked, high strength, commercially pure titanium having an ultimate tensile strength of at least about 900 MPa, the generally cylindrical body having a proximal portion and an opposing distal portion for anchoring the angled dental implant in bone of a patient, an exterior surface of the proximal portion of the generally cylindrical body including a thread;
 an interior bore formed in the generally cylindrical body, thereby forming a circumferentially extending wall defined by at least a portion of an outer surface of the generally cylindrical body and at least a portion of an inner surface of the interior bore, the interior bore having a bore-central axis that is at an angle between about 7° and about 31° relative to the main-central axis of the generally cylindrical body, the relative angle of the bore-central axis causing at least a first portion of the circumferentially extending wall to have a varying thickness about a circumference of the first portion, the thickness of the circumferentially extending wall at the first portion varying from a thinnest portion adjacent to a first side of the generally cylindrical body to a thickest portion adjacent to a second opposing side of the generally cylindrical body, the interior bore having a threaded portion for receiving a screw configured to removable hold an abutment in engagement with the angled dental implant, the thread of the exterior surface of the proximal portion of the generally cylindrical body being located about the first portion of the circumferentially extending wall having the thinnest portion; and
 a non-rotational feature configured to engage the abutment in a non-rotational fashion,
 wherein a ratio of the maximum outer diameter of the generally cylindrical body to the thinnest portion of the circumferentially extending wall adjacent to the first side of the generally cylindrical body at the first portion is between about 16 and about 80.

2. The angled dental implant of claim 1, wherein the first portion of the circumferentially extending wall is adjacent to a proximal end of the interior bore.

3. The angled dental implant of claim 1, wherein the first portion of the circumferentially extending wall is adjacent to a distal end of the interior bore.

4. The angled dental implant of claim 1, wherein the maximum outer diameter is about 3 millimeters, about 3.25 millimeters, about 3.5 millimeters, about 4 millimeters, or about 4.25 millimeters.

5. The angled dental implant of claim 1, wherein the thinnest portion of the circumferentially extending wall adjacent to the first side of the generally cylindrical body at the first portion is about 0.04 millimeters, about 0.10 millimeters, about 0.15 millimeters, about 0.2 millimeters, about 0.25 millimeters, about 0.3 millimeters, about 0.35 millimeters, or about 0.4 millimeters.

6. The angled dental implant of claim 1, wherein the angled dental implant is an internal-connection dental implant and the non-rotational feature includes a socket formed in the interior bore.

7. The angled dental implant of claim 1, wherein the angled dental implant is an external-connection dental implant and the non-rotational feature includes a boss extending from the proximal portion of the generally cylindrical body.

8. The angled dental implant of claim 1, wherein, prior to engaging the abutment, the non-rotational feature is configured to be engaged by a tool to install the angled dental implant into the bone of the patient.

9. The angled dental implant of claim 8, wherein the non-rotational feature is a six-sided hexagonal boss.

10. The angled dental implant of claim 8, wherein the non-rotational feature is a twelve-sided star-shaped boss.

11. The angled dental implant of claim 1, wherein the thread of the exterior surface of the proximal portion of the generally cylindrical body is a micro thread, and wherein an exterior surface of the opposing distal portion of the generally cylindrical body includes a main thread.

12. The angled dental implant of claim 11, wherein the micro thread has a smaller peak-to-trough distance and a larger minor thread diameter relative to the main thread.

* * * * *